United States Patent
Oh et al.

(10) Patent No.: US 11,884,750 B2
(45) Date of Patent: Jan. 30, 2024

(54) CATIONIC CELL PENETRATING PEPTIDES AND THE USE THEREOF

(71) Applicant: CELLTROY CO., LTD., Seoul (KR)

(72) Inventors: Chang-Kyu Oh, Seoul (KR); Jae-Ho Lee, Gyeonggi-do (KR); Soon-Ik Park, Gyeonggi-do (KR); Jeong-Ho Park, Gyeonggi-do (KR); Won-Jin Park, Seoul (KR); Yun-Chu Cho, Seoul (KR)

(73) Assignee: CELLTROY CO., LTD., Seoul (KR)

( * ) Notice: Subject to any disclaimer, the term of this patent is extended or adjusted under 35 U.S.C. 154(b) by 0 days.

(21) Appl. No.: 17/814,363

(22) Filed: Jul. 22, 2022

(65) Prior Publication Data
US 2023/0053924 A1    Feb. 23, 2023

Related U.S. Application Data

(60) Provisional application No. 63/230,929, filed on Aug. 9, 2021.

(51) Int. Cl.
*C07K 7/08* (2006.01)
*A61K 47/64* (2017.01)

(52) U.S. Cl.
CPC .............. *C07K 7/08* (2013.01); *A61K 47/64* (2017.08); *C07K 2319/10* (2013.01); *C07K 2319/60* (2013.01)

(58) Field of Classification Search
CPC ................. A61K 38/00; A61K 47/645; A61K 47/6455; A61K 38/10; A61P 35/00; C07K 2319/10; C07K 7/08; C07K 2319/00
See application file for complete search history.

(56) References Cited

U.S. PATENT DOCUMENTS 6,551,795 B1 *    4/2003    Rubenfield ............ C07K 14/21
                                                     435/6.15

FOREIGN PATENT DOCUMENTS

KR         101971021         4/2019

\* cited by examiner

*Primary Examiner* — Aradhana Sasan
*Assistant Examiner* — Jia-Hai Lee
(74) *Attorney, Agent, or Firm* — Riverside Law LLP

(57) ABSTRACT

A cell penetrating peptide (CPP) according to the present invention is a novel cationic cell penetrating peptide that can effectively transport a biologically active molecule by passing through a cell membrane even when a biologically active molecule is bound thereto, and compared with conventional CPPs, it has excellent cell permeability enabling the transport of a biologically active molecule into cells, and the delivered biologically active molecule may effectively maintain its activity in cells. Accordingly, the CPP of the present invention may be very useful in various fields including cosmetics, diagnostics, drug delivery systems, recombinant protein vaccines, DNA/RNA therapeutics, and gene and protein therapy.

15 Claims, 22 Drawing Sheets

Specification includes a Sequence Listing.

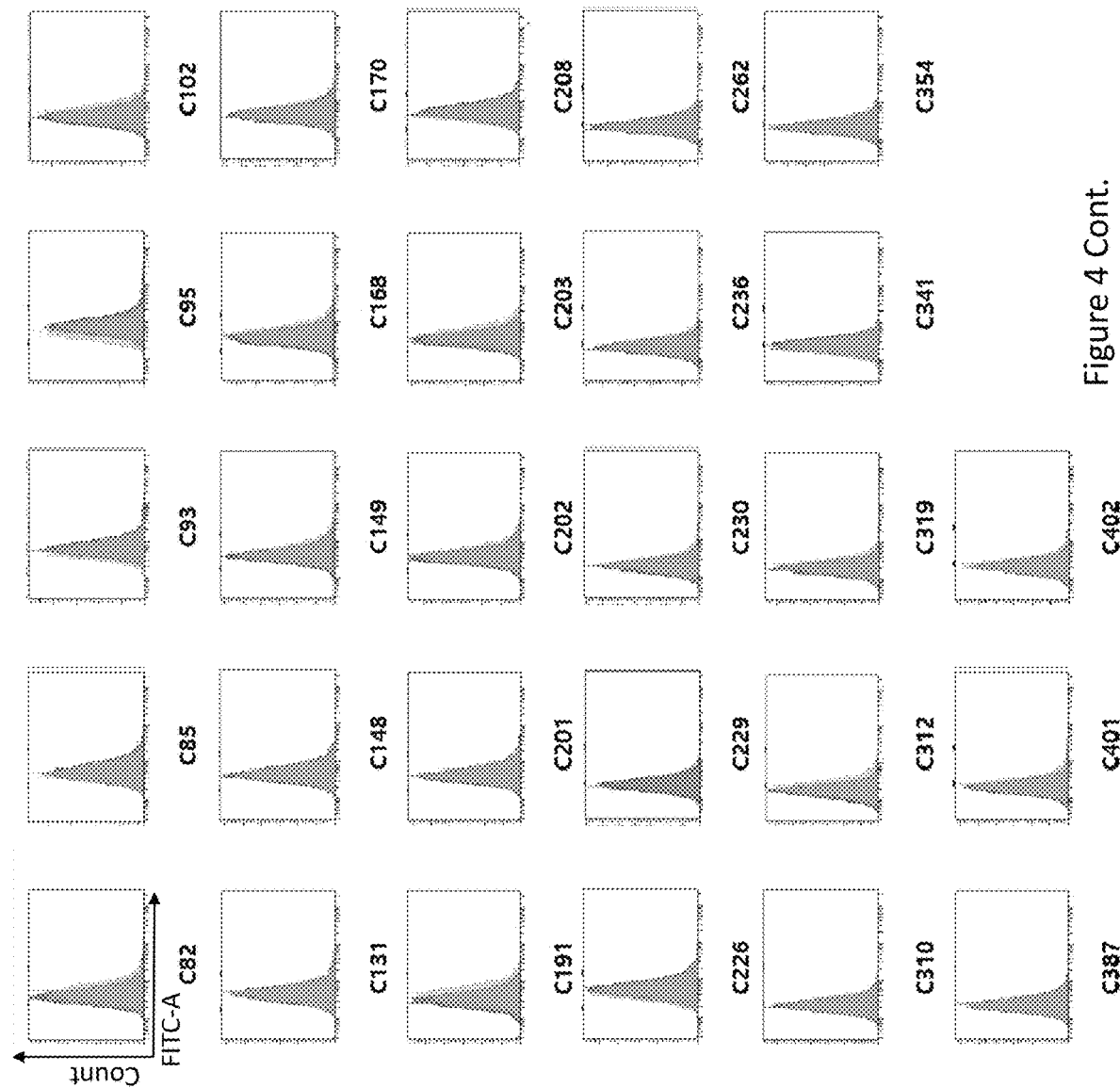

CATIONIC CELL PENETRATING PEPTIDES AND THE USE THEREOF

CROSS-REFERENCE TO RELATED APPLICATION

This application claims priority to and the benefit of U.S. provisional application No. 63/230,929, filed on Aug. 9, 2021, the disclosure of which is incorporated herein by reference in its entirety.

REFERENCE TO SEQUENCE LISTING SUBMITTED ELECTRONICALLY

This application contains a sequence listing, which is submitted electronically via Patent Center as an XML formatted sequence listing with a file name "206132_0119_00US_SequenceListing.xml", created on Jul. 21, 2022, file size of 65,792 bytes. The sequence listing submitted via Patent Center is part of the specification and is herein incorporated by reference in its entirety.

FIELD OF THE INVENTION

The present invention relates to intracellular delivery technology for delivering a biologically active molecule into cells, and more particularly, to a novel cationic cell penetrating peptide having more improved cell permeability compared with a conventional cell penetrating peptide, and a used thereof.

BACKGROUND

Discussion of Related Art

A cell membrane is a barrier to the intracellular penetration of proteins, nucleic acids, peptides and poorly soluble chemicals due to its inherent impermeability. The intracellular delivery of a drug is a problem that has to be solved in the fields of disease treatment, prevention, and diagnosis. Generally, methods for passing biologically active macromolecules through the cell membrane include electroporation, membrane fusion using a liposome, transfection using a cationic polymer, such as polyethyleneimine (PEI) or DEAE-dextran, viral nucleic acid infection, single cell microinjection, etc. In addition, recently, for effective intracellular drug delivery, technology that applies the endocytosis of a drug delivery system such as nanoparticles has been used, but more studies are needed because of toxicity, reduced delivery efficiency caused by rapid loss in the immune system, or steric hindrance caused by the interaction with cells. In order to solve this problem, recently, many attempts are being made to use a cell penetrating peptide (CPP).

CPP is a peptide generally consisting of 5 to 30 amino acids, and has a function transporting biologically active molecules such as liposomes, nucleic acids, proteins, or compounds into cells without a particular receptor. CPP was first known in 1988 when the human immunodeficiency virus (HIV) transcription factor TAT was confirmed to be transmitted into cells, and since then, various CPPs such as penetratin, VP22, and MTS have been developed. However, in the conventional CPPs, when a biologically active macromolecule, which is cargo, is bound thereto, the cell permeability, pattern, solubility, and structure of the peptide are changed so that the peptide cannot pass through the cell membrane or the activity of the biologically active molecule is not maintained. Due to these problems, the number of CPPs that can be substantially industrialized and used is insufficient. Therefore, if a novel CPP that can effectively transport cargo into cells through a cell membrane even when a biologically active macromolecule is bound thereto is developed, it is expected to be effectively applied to various fields such as beauty, diagnosis, and medical care.

RELATED ART DOCUMENT

Patent Document (Patent Document 1) Korean Patent No. 10-1971021

SUMMARY OF THE INVENTION

To solve the problems of the conventional art, the present invention is directed to providing a novel cell penetrating peptide (CPP) that is able to effectively transport a biologically active molecule into cells through a cell membrane even when the biologically active molecule is bound thereto, and a use thereof.

However, technical problems to be solved in the present invention are not limited to the above-described problems, and other problems which are not described herein will be fully understood by those of ordinary skill in the art from the following descriptions.

Technical Solution

The present invention provides a CPP consisting of an amino acid sequence represented by the following general formula:

$$R_1\text{-}R_2\text{-}R_3\text{-}R_4\text{-}R_5\text{-}R_6\text{-}R_7\text{-}R_8\text{-}R_9\text{-}R_{10}\text{-}R_{11}\text{-}R_{12}\text{-}R_{13}\text{-}R_{14} \quad \text{[General Formula]}$$

In General Formula, $R_{14}$ is arginine (R), proline (P), lysine (K), or isoleucine (i);

at least one of $R_1$ to $R_{14}$ is proline (P);

among $R_1$ to $R_{14}$, when arginine (R) is assigned 1 point and lysine (K) is assigned 0.5 points, the sum of the peptide is 6.5 points or more; and the peptide includes one or more amino acids selected from the group consisting of valine (V), leucine (L), and isoleucine (I).

In one embodiment of the present invention, the CPP may have an α-helix structure, but the present invention is not limited thereto.

In another embodiment of the present invention, the CPP may be cationic, but the present invention is not limited thereto.

In still another embodiment of the present invention, the peptide may further satisfy one or more selected from the group consisting of the following characteristics, but the present invention is not limited thereto:

(a) In the General Formula, $R_5$-$R_6$ is any one set of consecutive amino acids selected from the group consisting of VI, KR, RL, KK, LR, RA, RK, and KQ;

(b) $R_9$ and $R_{10}$ are each independently arginine (R), lysine (K), alanine (A), leucine (L), histidine (H), or tryptophan (W); and (c) $R_2$ is proline (P), leucine (L), arginine (R), lysine (K), valine (V), or alanine (A).

In yet another embodiment of the present invention, the peptide may further satisfy one or more selected from the group consisting of the following characteristics, but the present invention is not limited thereto:

(a) In General Formula, $R_4$ is lysine (K), leucine (L), arginine (R), or isoleucine (I); and (b) the peptide does not include glutamic acid (E), glycine (G), and tyrosine (Y).

In yet another embodiment of the present invention, the CPP may consist of any one amino acid sequence selected from the group consisting of SEQ ID NOs: 1 to 53, but the present invention is not limited thereto.

In yet another embodiment of the present invention, the CPP may mediate the transport of a biologically active molecule bound thereto, but the present invention is not limited thereto.

In yet another embodiment of the present invention, the cells may be one or more selected from the group consisting of blood-brain barrier endothelial cells, cancer cells, blood cells, epithelial cells, skin cells, epidermal cells, dermal fibroblasts, cervical cells, lymphocytes, immune cells, stem cells, induced pluripotent stem cells, neural stem cells, T cells, B cells, natural killer cells, macrophages, monocytes, microglia, neurons, glial cells, astrocytes, muscle cells, brain cells, hepatocytes, kidney cells, lung cells, and laryngeal cells, but the present invention is not limited thereto.

In addition, the present invention provides a polynucleotide encoding the CPP.

In addition, the present invention provides a complex including the CPP and a biologically active molecule.

In one embodiment of the present invention, the CPP may be bound to one end or both ends of the biologically active molecule, but the present invention is not limited thereto.

In another embodiment of the present invention, in the complex, one to five connected CPPs may be bound to one end or both ends of the biologically active molecule, but the present invention is not limited thereto.

In still another embodiment of the present invention, the binding may be a chemical bond, a bond with a linker, or a peptide bond, but the present invention is not limited thereto.

In yet another embodiment of the present invention, the chemical bond may be one or more selected from the group consisting of a disulfide bond, a diamine bond, a sulfide-amine bond, a carboxyl-amine bond, an ester bond, a diselenide bond, a maleimide bond, a thioester bond, and a thioether bond, but the present invention is not limited thereto.

In yet another embodiment of the present invention, the biologically active molecule may be one or more selected from the group consisting of peptides, proteins, glycoproteins, nucleic acids, carbohydrates, lipids, glycolipids, compounds, natural products, semi-synthetic drugs, microparticles, nanoparticles, liposomes, viruses, quantum dots, fluorochromes, and toxins, but the present invention is not limited thereto.

In yet another embodiment of the present invention, the protein may be one or more selected from the group consisting of growth factors, enzymes, nucleases, transcription factors, antigenic peptides, antibodies, antibody fragments, hormones, carrier proteins, immunoglobulins, structural proteins, motor function proteins, receptors, signaling proteins, storage proteins, membrane proteins, transmembrane proteins, internal proteins, external proteins, secretory proteins, viral proteins, protein complexes, chemically modified proteins, and prions, but the present invention is not limited thereto.

In yet another embodiment of the present invention, the nucleic acid may be one or more selected from the group consisting of DNA, RNA, an antisense oligonucleotide (ASO), microRNA (miRNA), small interfering RNA (siRNA), an aptamer, a locked nucleic acid (LNA), a peptide nucleic acid (PNA), and a morpholino, but the present invention is not limited thereto.

In yet another embodiment of the present invention, the compound may be one or more selected from the group consisting of a therapeutic drug, a toxic compound, and a chemical compound, but the present invention is not limited thereto.

In addition, the present invention provides a composition for delivering a biologically active molecule, which includes the CPP or the complex as an active ingredient.

In addition, the present invention provides a method of delivering a biologically active molecule into a subject or cells, which includes administering the complex into a subject or cells in need thereof. The method may comprise combining a biologically active molecule to the CPP.

In addition, the present invention provides a use of the CPP for delivering a biologically active molecule into cells.

In addition, the present invention provides a use of the CPP for preparing a drug for delivering a biologically active molecule.

In addition, the present invention provides a use of the CPP for preparing a drug with improved cell permeability.

In addition, the present invention provides a CPP selecting method, which includes the following steps:

(S1) preparing a 10- to 20-mer peptide library derived from a transcription factor protein; and (S2) selecting a peptide satisfying one or more of the following conditions from among the peptides obtained in (S1):

(i) when arginine (R) is assigned 1 point and lysine (K) is assigned 0.5 points, the sum of the peptide is 6.5 points or more;

(ii) at least one proline (P) is included; and (iii) at least one hydrophobic amino acid is included.

In one embodiment of the present invention, the method may further include (S3) selecting a peptide having an α-helix structure from among the peptides selected in (S2), but the present invention is not limited thereto.

In another embodiment of the present invention, the hydrophobic amino acid of (iii) may be one or more selected from the group consisting of valine (V), leucine (L), isoleucine (I), phenylalanine (F), and methionine (M), but the present invention is not limited thereto.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
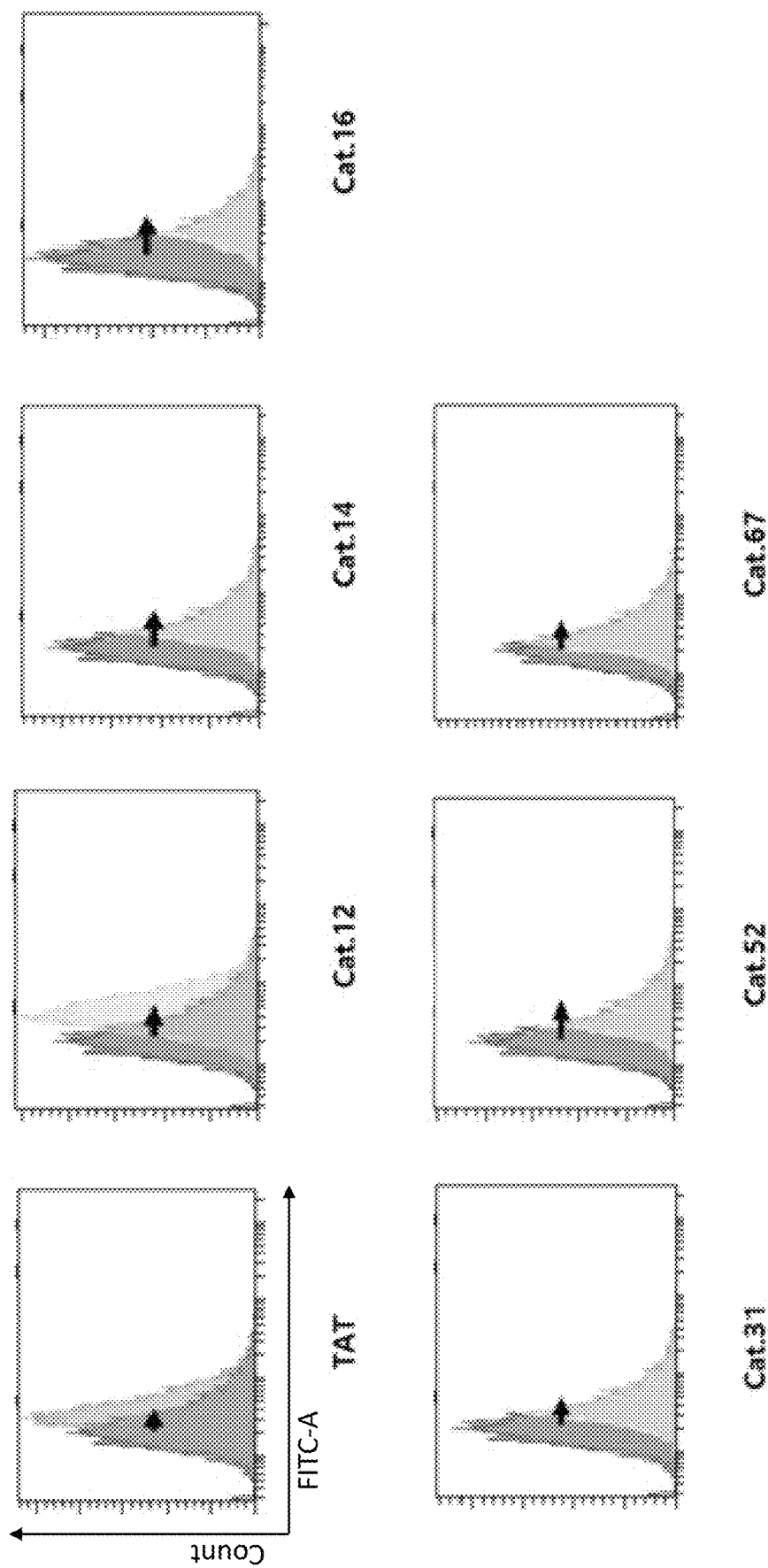
FIG. 1 shows a result of confirming the cell penetration efficiency of cationic cell penetrating peptides (CPPs) according to one embodiment of the present invention using human epidermal cells.

The present invention is directed to providing a novel cationic cell penetrating peptide capable of effectively transporting a biologically active molecule into cells through a cell membrane even when the biologically active molecule is bound thereto and a use thereof.

Specifically, in one embodiment of the present invention, novel cationic cell penetrating peptides (cationic CPPs (hereinafter, referred to as "CPPs")) having higher cell permeability, compared with conventionally known CPPs, were selected by screening a known transcription factor protein sequence as a whole, selecting peptides satisfying specific conditions, including a length and properties, and confirming the cell permeability thereof (Example 1).

In another embodiment of the present invention, as a result of evaluating the cell penetration efficiency of a biologically active material-bound CPP in human epidermal cells and neuroblastoma cells, it was confirmed that the cell penetration efficiency of the CPPs of the present invention is significantly higher than that of the conventional CPPs (Example 2).

In still another embodiment of the present invention, as a result of confirming whether the CPP substantially delivers the biologically active molecule into cells, the CPP more effectively delivers the biologically active molecule into cells, compared with the conventional CPP, and it was confirmed that the active molecule delivered into cells by the CPP maintains biological activity and functions (Example 3).

In yet another embodiment of the present invention, as a result of confirming cell permeability by additionally synthesizing the selected peptides in the examples in order to additionally select CPP having excellent cell permeability, it was confirmed that the CPPs exhibit excellent cell permeability (Example 4).

In yet another embodiment of the present invention, by measuring the cell permeability of the CPPs according to the present invention in various types of cells, it was confirmed that the CPPs according to the present invention exhibits excellent biologically active molecule delivery efficiency, compared with the conventional CPPs, in various cells/tissues (Example 5).

Accordingly, it has been verified that the novel cationic CPP according to the present invention can exhibit excellent cell permeability, biologically active molecule delivery efficiency, and the capacity to maintain the activity of a biologically active molecule in various tissues and cells, and thus is expected to be useful in various industrial fields, including cosmetics, diagnosis, vaccines, and therapeutics.

Hereinafter, the present invention will be described in detail.

One letter (three letters) of amino acids used in the specification refers to the following amino acids according to the standard abbreviation rules in the field of biochemistry: A (Ala), alanine; C (Cys), cysteine; D (Asp), aspartic acid; E (Glu), glutamic acid; F (Phe), phenylalanine; G (Gly), glycine; H (His), histidine; I (He), isoleucine; K (Lys), lysine; L (Leu), leucine; M (Met), methionine; N (Asn), asparagine; O (Ply), pyrrolysine; P (Pro), proline; Q (Gln), glutamine; R (Arg), arginine; S (Ser), serine; T (Thr), threonine; U (Sec), selenocysteine; V (Val), valine; W (Trp), tryptophan; and Y (Tyr), tyrosine.

The present invention provides CPP consisting of an amino acid sequence represented by the following General Formula:

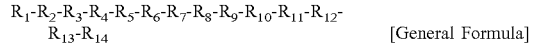

$R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$ [General Formula]

In General Formula, $R_{14}$ is arginine (R), proline (P), lysine (K), or isoleucine (I);

at least one of $R_1$ to $R_{14}$ is proline (P);

among $R_1$ to $R_{14}$, when arginine (R) is assigned 1 point and lysine (K) is assigned 0.5 points, the sum of the peptide is 6.5 points or more; and the peptide includes one or more hydrophobic amino acids selected from the group consisting of valine (V), leucine (L), isoleucine (I), phenylalanine (F), and methionine (M).

Unless stated otherwise, throughout the specification, the amino acid sequence is described in a direction from N- to C-termini.

In the present invention, the "cell permeability" refers to an ability or property of a material to penetrate into cells through a cell membrane. The "cell membrane" used herein refers to a lipid-containing barrier that separates cells or cell populations from the extracellular space. The cell membrane includes a plasma membrane, a cell wall, or an intracellular organelle membrane, such as the mitochondrial membrane and the nuclear membrane, but the present invention is not limited thereto.

As the "peptide" used herein refers to a polymer of amino acids, generally, a form of several connected hydrophobic amino acids is called a peptide, and when many amino acids are connected, it is called a protein. In a peptide or protein structure, the linkage between amino acids consists of amide bonds or peptide bonds. A peptide bond refers to a bond making a —CO—NH— form by the release of water ($H_2O$) between a carboxyl group (—COOH) and an amino group (—$NH_2$).

The "cell penetrating peptide (CPP)" used herein refers to a peptide with cell permeability, which is an ability to deliver cargo into cells in vitro and/or in vivo.

The "cargo" used herein includes all materials which are able to be bonded with CPP, move into cells, and includes all types of biologically active molecules without limitation. The cargo includes, for example, all materials that need to increase cell penetration efficiency, specifically, effective materials of drugs, cosmetics or health food, more specifically, materials that are not easy to move into cells through a common route, and even more specifically, proteins, nucleic acids, peptides, minerals, sugars such as glucose, nanoparticles, biological agents, viruses, contrast materials, or other chemicals, but the present invention is not limited thereto. They can be included without limitation as long as they can move into cells and exhibit biological activity.

Preferably, the CPP according to the present invention is a transcription factor protein-derived peptide. More preferably, the transcription factor protein is a Sus scrofa transcription factor protein.

The CPP according to the present invention may further include various amino acids at the N-terminus and/or C-terminus, in addition to the amino acids of $R_1$ to $R_{14}$. Alternatively, in the CPP according to the present invention, one or more amino acids may be deleted from the N-terminus and/or C-terminus of the amino acids of $R_1$ to $R_{14}$. That is, the CPP according to the present invention may include addition and/or deletion of some amino acids as long as its properties and functions are maintained.

Therefore, the CPP preferably consists of 14 amino acids as a whole, but more preferably consists of 7 to 25, 7 to 24, 7 to 23, 7 to 22, 7 to 21, 7 to 20, 7 to 19, 7 to 18, 7 to 17, 7 to 16, 7 to 15, 7 to 14, 7 to 13, 7 to 12, 7 to 11, 7 to 10, 7 to 9, 9 to 24, 9 to 22, 9 to 20, 9 to 19, 9 to 18, 9 to 17, 9 to 16, 9 to 15, 9 to 14, 9 to 13, 9 to 12, 9 to 11, 11 to 24, 11 to 22, 11 to 20, 11 to 19, 11 to 18, 11 to 17, 11 to 16, 11 to 15, 11 to 14, 12 to 15, or 13 to 15 amino acids.

In addition, a part or all of the CPP according to the present invention may have an α-helix structure.

In addition, the CPP according to the present invention may be a cationic peptide. That is, the CPP may have a positive charge as a whole.

In the scope of the present invention, derivatives and analogs (mimetics or peptidomimetics) of the CPP are included. The "derivatives" encompass similar peptides obtained by changing some amino acids of the CPP according to the present invention, and preferably, include those in which one or more amino acids are substituted, those in which one or more amino acids are added, those in which one or more amino acids are deleted, or those fused with a compound increasing the half-life of the peptide (e.g., polyethylene glycol). In the present invention, the derivatives may maintain, increase or decrease the functions or characteristics (e.g., cell permeability) of the CPP according to the present invention.

More specifically, the derivatives may have the substitution of one or more amino acid while maintaining the characteristics as the CPP according to the present invention. The amino acid substitution may occur, generally, based on similarity in polarity, charge, solubility, hydrophobicity, hydrophilicity and/or amphipathic nature of residues. For example, as conservative or semi-conservative substitution, glycine, alanine, valine, leucine, and isoleucine having an aliphatic side chain may be substituted for each other; glycine and alanine having a relatively short side chain may be substituted for each other; valine, leucine, and isoleucine, which have an aliphatic side chain with higher hydrophobicity, may be substituted for each other; phenylalanine, tyrosine, and tryptophan having an aromatic side chain may be substituted for each other; lysine, arginine, and histidine having a basic side chain may be substituted for each other; aspartate and glutamate having an acidic side chain may be substituted for each other; and cysteine and methionine having a sulfur-containing side chain may be substituted for each other.

Preferably, the CPP according to the present invention may include any one amino acid sequence selected from the group consisting of SEQ ID NOs: 1 to 53, more preferably, consist of any one amino acid sequence selected from the group consisting of SEQ ID NOs: 1 to 53, but the present invention is not limited thereto. Variants of the amino acid sequence are included in the scope of the present invention. That is, the CPP of the present invention is a concept including functional equivalents of a polypeptide constituting the same, for example, variants in which a part of the amino acid sequence of the polypeptide is modified through deletion, substitution or insertion, but capable of having functionally the same action as the polypeptide. For example, the CPP according to the present invention may include an amino acid sequence having 70% or more, more preferably, 80% or more, even more preferably 90% or more, and most preferably 95% or more sequence homology with any one amino acid sequence selected from the group consisting of SEQ ID NOs: 1 to 53. For example, the CPP of the present invention includes a polypeptide having 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and 100% sequence homology. The "% sequence homology" with a polypeptide is identified by comparing two optimally-arranged sequences and a comparative region, and a part of the polypeptide sequence in the comparative region may have an addition or deletion (i.e., gap) compared to a reference sequence for the optimal arrangement of two sequences (not including addition or deletion).

The CPP according to the present invention may further satisfy one or more selected from the group consisting of the following characteristics:
(a) In General Formula, $R_5$-$R_6$ are any one set of consecutive amino acids selected from the group consisting of VI, KR, RL, KK, LR, RA, RK, and KQ;
(b) $R_9$ and $R_{10}$ are each independently arginine (R), lysine (K), alanine (A), leucine (L), histidine (H), or tryptophan (W);
(c) $R_2$ is proline (P), leucine (L), arginine (R), lysine (K), valine (V), or alanine (A);
(d) in General Formula, $R_4$ is lysine (K), leucine (L), arginine (R), or isoleucine (I); and/or (e) the peptide does not include glutamic acid (E), glycine (G), and tyrosine (Y).

The present inventors confirmed from specific embodiments that CPPs satisfying the above-described characteristics exhibit greater cell permeability, compared with the conventional CPPs, in various tissues or various types of cells (normal or cancer cells), such as human epidermal cells, neuroblastoma cells, macrophages, monocytes, brain cells, skin cells, cervical cells, hepatocytes, kidney cells, lung cells, and laryngeal cells. That is, as the CPP according to the present invention, since the peptides satisfying the characteristics described herein have excellent cell permeability regardless of the type of cells or tissue, biologically active materials may be delivered by targeting a variety of cells and tissue.

Most preferably, the CPP according to the present invention may include any one amino acid sequence selected from the group consisting of SEQ ID NOs: 1 to 16 (C12, C14, C16, C31, C52, C67, C93, C95, C113, C179, C185, C12, C14, C16, C31, C52, C67, C93, C95, C113, C179, and C185 in order), more preferably, may consist of any one amino acid sequence selected from the group consisting of SEQ ID NOs: 1 to 16, and may include an amino acid sequence with 70% or more, more preferably 80% or more, even more preferably 90% or more, and most preferably 95% or more sequence homology with any one amino acid sequence selected from the group consisting of SEQ ID NOs: 1 to 16. For example, the CPP according to the present invention includes a polypeptide having 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence homology.

The CPP according to the present invention has increased cell permeability, compared with TAT, which is CPP according to the related art. The "increased cell permeability" may mean that the cell permeability is at least 1%, 2%, 3%, 4%, 5%, 10% or more, for example, 5%, 10%, 20%, 30%, 40%, or 50%, 60%, 70%, 80%, 90% or higher, and/or 0.5-, 1.1-, 1.2-, 1.4-, 1.6-, 1.8-, 1.9-, 2-fold higher than the control (TAT), but the present invention is not limited thereto. More specifically, the CPP according to the present invention may have 1.01 to 10-, 1.1 to 10-, 1.5 to 8-, 1.5 to 5-, 1.9 to 10-, 1.9 to 8-, or 1.9 to 5-fold greater cell permeability, compared with TAT.

In addition, the CPP according to the present invention may more effectively deliver a biologically active material by exhibiting more excellent cell permeability in specific cells or tissue.

Specific types of the cells are not limited, and are preferably selected from epidermal cells, macrophages, monocytes, brain cells, skin cells, cervical cells, skin cells, epithelial cells, fibroblasts, connective tissue cells, hepatocytes, kidney cells, lung cells, laryngeal cells, and various cancer cells.

Specifically, the CPP according to the present invention is CPP consisting of an amino acid sequence represented by the following general formula, and the cells may be macrophages:

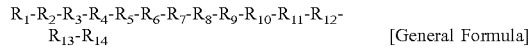

[General Formula]

In General Formula, $R_{14}$ is arginine (R), proline (P), lysine (K), or isoleucine (I);

at least one of $R_1$ to $R_{14}$ is proline (P);

among $R_1$ to $R_{14}$, when arginine (R) is assigned 1 point and lysine (K) is assigned 0.5 points, the sum of the peptide is 6.5 points or more; and the peptide includes one or more amino acids selected from the group consisting of valine (V), leucine (L), and isoleucine (I).

Most preferably, the macrophage penetrating peptide may consist of any one amino acid sequence selected from the group consisting of SEQ ID NOs: 1, 3, 4, 5, 8, 9, 10, 11, 12, 14, 18, 20, 23, 27, and 28.

In addition, the CPP according to the present invention may be CPP consisting of the amino acid represented by the above General Formula, and the cell may be monocytes. Most preferably, the monocyte penetrating peptide may consist of any one amino acid sequence selected from the group consisting of SEQ ID NOs: 7 to 19, 22, 23, 27, 34, and 39.

In addition, the CPP according to the present invention may be CPP consisting of the amino acid sequence represented by the above General Formula, and the cells may be brain cells or brain tumor cells. The brain tumor may be neuroblastoma or glioblastoma. Most preferably, the brain cell or brain tumor (neuroblastoma) CPP may consist of any one amino acid sequence selected from the group consisting of SEQ ID NOs: 1 to 21, 28, 29, 33 to 42, 45, 49, 51, and 53. Alternatively, the brain cell or brain tumor (glioblastoma) penetrating peptide may consist of any one amino acid sequence selected from the group consisting of SEQ ID NOs: 1, 2, 3, 6 to 15, 19, 20, 21, 27, 28, 29, 33, 37, 38, 39, 40, 41, 47, 49, and 50.

In addition, the CPP according to the present invention may be CPP consisting of the amino acid sequence represented by the above General Formula. More preferably, the cells may be epidermal cells (or keratinocytes), or dermal fibroblasts. Most preferably, the skin cell (keratinocytes) penetrating peptide may consist of any one amino acid sequence selected from the group consisting of SEQ ID NOs: 2 to 18, 23, and 33. Alternatively, the skin cell (dermal fibroblasts) penetrating peptide nay consist of any one amino acid sequence selected from the group consisting of SEQ ID NOs: 2 to 16, 18, 19, 38, and 39.

In addition, the CPP according to the present invention may be CPP consisting of an amino acid sequence represented by the above General Formula, and the cells may be cervical cells or cervical cancer cells. Most preferably, the cervical cell or cervical cancer cell penetrating peptide may consist of any one amino acid sequence selected from the group consisting of SEQ ID NOs: 1 to 7, 9 to 16, 19 to 31, 38, 39, 41 to 46, 48 to 51, and 53.

In addition, the CPP according to the present invention may be CPP consisting of an amino acid sequence represented by the above General Formula, and the cells may be connective tissue cells or fibrosarcoma cells. Preferably, the connective tissue cells may be epithelial cells. Most preferably, the connective tissue cell or fibrosarcoma cell penetrating peptide may consist of any one amino acid sequence selected from the group consisting of SEQ ID NOs: 1 to 7, 9, 10, 12, 13, 15, 16, 17, 18, 21, 25, 26, 27, 29, 32, 46, 49, 52, 53, and 69.

In addition, the CPP according to the present invention may be CPP consisting of an amino acid sequence represented by the above General Formula, and the cells may be liver cells or liver cancer cells. Most preferably, the liver cell or liver cancer cell penetrating peptide may consist of any one amino acid sequence selected from the group consisting of SEQ ID NOs: 1 to 14.

In addition, the CPP according to the present invention may be CPP consisting of an amino acid sequence represented by the above General Formula, and the cells may be kidney cells or kidney cancer cells. Most preferably, the kidney cell or kidney cancer cell penetrating peptide may consist of any one amino acid sequence selected from the group consisting of SEQ ID NOs: 1 to 12, 24 to 29, and 45 to 51.

In addition, the CPP according to the present invention may be CPP consisting of an amino acid sequence represented by the above General Formula, and the cells may be lung cells or lung cancer cells. Most preferably, the lung cell or lung cancer cell penetrating peptide may consist of any one amino acid sequence selected from the group consisting of SEQ ID NOs: 1 to 10, 12, 15, 17, 26, 29, 32, 46, 52, and 53.

In addition, the CPP according to the present invention may be CPP consisting of an amino acid sequence represented by the above General Formula, and the cells may be laryngeal cells or laryngeal cancer cells. Preferably, the laryngeal cancer may be laryngeal squamous cell carcinoma. Most preferably, the laryngeal cell or laryngeal cancer cell penetrating peptide may consist of any one amino acid sequence selected from the group consisting of SEQ ID NOs: 1 to 16, 18, 20, 23, 27, and 30.

In addition, the present invention provides a CPP screening method, which includes the following step:

(S1) preparing a 10- to 20-mer peptide library derived from a transcription factor protein; and (S2) selecting a peptide satisfying one or more of the following conditions from among the peptides obtained in (S1):

(i) when arginine (R) is assigned 1 point and lysine (K) is assigned 0.5 points, the sum of the peptide is 6.5 points or more;

(ii) at least one proline (P) is included;

(iii) at least one hydrophobic amino acid is included; and (iv) the amino acid at the C-terminus of the peptide is arginine (R), proline (P), lysine (K), or isoleucine (I).

That is, those of ordinary skill in the art may select CPP exhibiting excellent cell permeability in various cells through a screening method according to the present invention.

In the screening method, the 10 to 20-mer peptide (that is, a peptide consisting of 10 to 20 amino acids) library is a candidate peptide library of the CPP according to the present invention, which may be a group of 10 to 20-mer peptides obtained by randomly cutting a transcription factor protein to a length of 10 to 20 mer, but the present invention is not limited thereto. The preparation of the library may be performed according to a protein library preparation technology known in the art, and preferably, a python script, but the present invention is not limited thereto. The peptide may have a length of 10 to 20 mer, 10 to 18 mer, 10 to 16 mer, 10 to 15 mer, 12 to 20 mer, 12 to 15 mer, or 13 to 15 mer, and most preferably 14 mer, but the present invention is not limited thereto.

In addition, the screening method may further include selecting a peptide further satisfying one or more characteristics selected from the group consisting of the following characteristics after (S2):

(a) the $5^{th}$ to $6^{th}$ amino acids from the N-terminus of the peptide are any one set of consecutive amino acids selected from the group consisting of VI, KR, RL, KK, LR, RA, RK, and KQ;

(b) the $9^{th}$ and $10^{th}$ amino acids from the N-terminus of the peptide are each independently arginine (R), lysine (K), alanine (A), leucine (L), histidine (H), or tryptophan (W);

(c) the $2^{nd}$ amino acid from the N-terminus of the peptide is proline (P), leucine (L), arginine (R), lysine (K), valine (V), or alanine (A);

(d) the $4^{th}$ amino acid from the N-terminus of the peptide is lysine (K), leucine (L), arginine (R), or isoleucine (I); and (e) the peptide does not include glutamic acid (E), glycine (G), and tyrosine (Y).

The CPP according to the present invention may be screened by the screening method according to the present invention.

In one embodiment, the screening method according to the present invention may further include selecting a peptide with an α-helix structure from among (all or a part of) the peptides selected in (S2), but the present invention is not limited thereto.

In the screening method, the hydrophobic amino acid in (iii) may be one or more selected from the group consisting of valine (V), leucine (L), isoleucine (I), phenylalanine (F), and methionine (M), and more preferably, one or more selected from the group consisting of valine (V), leucine (L), and isoleucine (I), but the present invention is not limited thereto.

In addition, the screening method may further include measuring the cell penetration activity of the peptides selected in (S2). The measurement of the cell penetration activity of the peptides may use a method of measuring cell penetration activity known in the art without limitation. In one embodiment, the measurement of the cell penetration activity may be performed using the C3pred program. Further, the screening method may further include comparing the cell permeability of the selected CPPs with TAT.

In the present invention, the transcription factor protein may be any transcription factor protein known in the art. That is, the screening method is for finding CPPs exhibiting excellent cell permeability by selecting only peptides satisfying specific characteristics among the peptides with a length of 10 to 20 mer, or 14 mer, which are obtained by randomly cutting the known transcription factor protein.

In one embodiment of the present invention, the transcription factor protein may be a Sus scrofa transcription factor protein, but the present invention is not limited thereto.

Since the CPP according to the present invention itself has cell permeability, it can be used as a carrier that can effectively introduce any material bound to the peptide into cells.

In the present invention, specific types of the cells are not limited, and may be selected from, for example, blood-brain barrier endothelial cells, cancer cells, blood cells, epithelial cells, skin cells, epidermal cells, dermal fibroblasts, cervical cells, lymphocytes, immune cells, stem cells, induced pluripotent stem cells, neural stem cells, T cells, B cells, natural killer cells, macrophages, monocytes, microglia, neurons, glial cells, astrocytes, muscle cells, brain cells, hepatocytes, kidney cells, lung cells, and laryngeal cells.

In addition, the CPP according to the present invention has excellent cell permeability with respect to various types of cancer cells. In the present invention, the "cancer" refers to or describes a physiological condition typically characterized by uncontrolled cell growth in mammals, and may include, without limitation, life-threatening malignant tumors that rapidly grow while infiltrating surrounding tissues and spread or metastasize to each part of the body. Examples of cancer include carcinoma, lymphoma, blastoma, sarcoma, leukemia, and lymphoid malignancy, but the present invention is not limited thereto. More specific examples of cancer include breast cancer, chronic myelogenous leukemia, acute myeloid leukemia, chronic lymphocytic leukemia, acute lymphocytic leukemia, lung cancer, stomach cancer, colon cancer, bone cancer, pancreatic cancer, skin cancer, head cancer, head and neck cancer, melanoma, uterine cancer, ovarian cancer, colorectal cancer, small intestine cancer, rectal cancer, perianal cancer, fallopian tube carcinoma, endometrial cancer, cervical cancer, vaginal cancer, vulvar cancer, Hodgkin's disease, esophageal cancer, liver cancer, lymph adenocarcinoma, bladder cancer, gallbladder cancer, endocrine adenocarcinoma, prostate cancer, adrenal cancer, soft tissue sarcoma, urethral cancer, penile cancer, lymphocytic lymphoma, kidney cancer, ureter cancer, renal pelvic cancer, blood cancer, brain cancer (brain tumor), central nervous system tumors, spinal cord tumors, brainstem glioma, neuroblastoma, glioblastoma, pituitary adenoma, fibrosarcoma, laryngeal cancer, and laryngeal squamous cell carcinoma.

In addition, the present invention provides a polynucleotide encoding the CPP according to the present invention, and a recombinant vector including the polynucleotide.

In the present invention, the polynucleotide may include any one nucleic acid sequence selected from the group consisting of SEQ ID NOs: 62 to 74, or consist of the any one nucleic acid sequence, but the present invention is not limited thereto. That is, the sequence is merely an exemplary embodiment of the present invention, and the polynucleotide according to the present invention may include, without limitation, one that can result in producing the CPP according to the present invention through transcription and translation.

In the present invention, the polynucleotide may be formed as RNA or DNA, wherein the DNA includes cDNA and synthetic DNA. The DNA may be single- or double-stranded. If the DNA is double-stranded, it may be a coding strand or non-coding (antisense) strand, and the coding sequence encodes the same polypeptide as a result of the degeneracy or redundancy of the genetic code.

The polynucleotide of the present invention may also include a variant of the above-described polynucleotide, and the variant of the polynucleotide may be a naturally-occurring allelic variant of the polynucleotide or a non-naturally-occurring variant of the polynucleotide. The allelic variant is an alternate form of a polynucleotide sequence that can have the substitution, deletion, or addition of one or more nucleotides, which does not substantially change the function of an encoded polynucleotide. A single amino acid may be encoded by one or more nucleotide codons, and it is well known in the art that the polynucleotide can be easily modified to prepare an alternating polynucleotide encoding the same peptide.

For example, the polynucleotide according to the present invention may include a nucleic acid sequence having 70% or more, more preferably, 80% or more, and even more preferably 90% or more, and most preferably 95% or more sequence homology with any one nucleic acid sequence selected from the group consisting of SEQ ID NOs: 62 to 74. For example, the polynucleotide according to the present invention includes a polynucleotide having 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and 100% sequence homology.

In addition, the present invention provides a complex including the CPP according to the present invention and a biologically active molecule.

In addition, the present invention provides a method of preparing a biologically active molecule with cell permeability, which includes attaching (binding) the CPP according to the present invention to the biologically active molecule.

The "biologically active molecule" used herein preferably encompasses materials having biological or pharmaceutical activity, and refers to a material that can be involved in the regulation of physiological activity or express a pharmacological effect by intracellular penetration (into the cytoplasm or nucleus) or has biological activity even in various body parts, such as in cells, tissue, interstitial cells, and blood by being delivered thereinto and acting upon. Such a biologically active molecule may be used interchangeably with the term "macromolecule."

The biologically active molecule may be selected from the group consisting of peptides, proteins, glycoproteins, nucleic acids, carbohydrates, lipids, glycolipids, compounds, natural products, semi-synthetic drugs, microparticles, nanoparticles, liposomes, viruses, quantum dots, fluorochromes, toxins, and complexes thereof.

Non-limiting examples of the proteins include growth factors, enzymes, nucleases, transcription factors, antigenic peptides, antibodies, antibody fragments, hormones, carrier proteins, immunoglobulins, structural proteins, motor function proteins, receptors, signaling proteins, storage proteins, membrane proteins, transmembrane proteins, internal proteins, external proteins, secretory proteins, viral proteins, protein complexes, chemically modified proteins, and prions. The nuclease includes CRISPR-associated protein 9 (CAS9), CAS12, CAS13, CAS14, CAS variants, Cxx-C finger protein-1 (Cfp1), zinc-finger nucleases (ZEN), and transcription activator-like effector nuclease (TALEN).

Non-limiting examples of the nucleic acids include DNA, RNA, antisense oligonucleotides (ASOs), microRNA (miRNA), small interfering RNA (siRNA), aptamers, locked nucleic acids (LNAs), peptide nucleic acids (PNAs), and a morpholino.

Non-limiting examples of the compounds include therapeutic drugs, toxic compounds, and chemical compounds. The "drug" is a broad concept that includes materials for alleviating, prevention, treating, or diagnosing a disease, wound or specific symptom. That is, the CPP according to the present invention may be used as a carrier of a drug for preventing or treating a disease.

In addition, in the biologically active molecule of the present invention, cholesterol, chemotherapeutics, vitamins, co-factors, 2,5-A chimeras, allozymes, aptamers, and a molecule capable of regulating pharmacokinetics and/or pharmacodynamics of polymers such as polyamines, polyamides, polyethylene glycol, and polyether may be included.

The complex according to the present invention includes all of a simple mixture of a peptide and a material, a compound of a peptide and a material, and a product formed by linkage or conjugation by a chemical bond. In addition, the complex may be linked by a physical bond, a chemical bond, a covalent bond, a non-covalent bond, a peptide bond, or self-assembly, or linked in an integrated or fused form using a mediator (e.g., a linker).

Preferably, the chemical bond may be selected from the group consisting of a disulfide bond, a diamine bond, a sulfide-amine bond, a carboxyl-amine bond, an ester bond, a diselenide bond, a maleimide bond, a thioester bond, and a thioether bond, but the present invention is not limited thereto.

In addition, the CPP according to the present invention may be bound to one or both ends of the biologically active molecule. In addition, in the complex, one or a plurality of CPPs may be bound to one or both ends of the biologically active molecule. That is, in the complex, 1 to 5, 1 to 4, 2 to 3, 1 to 2, 2 to 5, 2 to 4, 2 to 3, 3 to 5, or 3 to 4 CPPs are connected and bound to one or both ends of the biologically active molecule.

The complex may be a complex produced by expressing the peptide and the biologically active material in a fusion state. For example, after inserting a gene encoding the peptide and a gene expressing the biologically active material into the vector, when an organism is transformed with the vector to express the gene inserted into the vector, the peptide and the biologically active material may be expressed as a fusion protein. When expressed as a fusion protein, any linker may be included between the peptide and the biologically active material.

In addition, the present invention provides a composition for delivering a biologically active molecule, which includes the complex according to the present invention as an active ingredient. The composition includes a pharmaceutical composition, a food composition, a health functional food composition, a cosmetic composition, and/or a feed composition.

The composition according to the present invention may include a complex including a pharmaceutically, sitologically, or veterinary acceptable salt of the CPP, and a biologically active molecule as an active ingredient. That is, in the scope of the CPP of the present invention, all isomers, hydrates and solvates that can be prepared by conventional methods, as well as pharmaceutically/sitologically/veterinary acceptable salts, may be included.

Examples of suitable acids may include hydrochloric acid, hydrobromic acid, sulfuric acid, nitric acid, perchloric acid, fumaric acid, maleic acid, phosphoric acid, glycolic acid, lactic acid, salicylic acid, succinic acid, toluene-p-sulfonic acid, tartaric acid, acetic acid, citric acid, methanesulfonic acid, formic acid, benzoic acid, malonic acid, gluconic acid, naphthalene-2-sulfonic acid, and benzenesulfonic acid. Acid addition salts may be prepared by conventional methods, for example, by dissolving the compound in an aqueous solution of an excess of acid and precipitating the salt using a water-miscible organic solvent such as methanol, ethanol, acetone or acetonitrile. Alternatively, such acid addition salts may be prepared by heating an equimolar amount of the compound and an acid or alcohol in water and then evaporating the mixture to dry, or suctioning the precipitated salt.

Salts derived from suitable bases may include alkali metals such as sodium and potassium, alkaline earth metals such as magnesium, and ammonium, but the present invention is not limited thereto. The alkali metal or alkaline earth metal salt may be obtained by, for example, by dissolving the compound in an excess alkaline metal hydroxide or alkaline earth metal hydroxide solution, filtering an undissolved compound salt, and then evaporating and drying the filtrate. Here, as the metal salt, particularly, a sodium, potassium or calcium salt is pharmaceutically suitable, and a silver salt corresponding thereto may be obtained by reacting an alkali metal or alkaline earth metal salt with a suitable silver salt (e.g., silver nitrate).

The scope of the peptide of the present invention may include all isomers, hydrates, and solvates that can be prepared by conventional methods as well as pharmaceutically acceptable salts.

The amount of the peptide or the complex in the composition of the present invention may be appropriately adjusted depending on the symptoms of a disease, the degree of progression of symptoms, the condition of a patient, and the like, and may range from, for example, 0.0001 wt % to 99.9 wt % or 0.001 wt % to 50 wt % with respect to a total weight of the composition, but the present invention is not limited thereto. The amount ratio is a value based on the amount of dried product from which a solvent is removed.

The pharmaceutical composition according to the present invention may further include a suitable carrier, excipient, and diluent which are commonly used in the preparation of pharmaceutical compositions. The excipient may be, for example, one or more selected from the group consisting of a diluent, a binder, a disintegrant, a lubricant, an adsorbent, a humectant, a film-coating material, and a controlled release additive.

The pharmaceutical composition according to the present invention may be used by being formulated, according to commonly used methods, into a form such as powders, granules, sustained-release-type granules, enteric granules, liquids, eye drops, elixirs, emulsions, suspensions, spirits, troches, aromatic water, lemonades, tablets, sustained-release-type tablets, enteric tablets, sublingual tablets, hard capsules, soft capsules, sustained-release-type capsules, enteric capsules, pills, tinctures, soft extracts, dry extracts, fluid extracts, injections, capsules, perfusates, or a preparation for external use, such as plasters, lotions, pastes, sprays, inhalants, patches, sterile injectable solutions, or aerosols. The preparation for external use may have a formulation such as creams, gels, patches, sprays, ointments, plasters, lotions, liniments, pastes, or cataplasmas.

As the carrier, the excipient, and the diluent that may be included in the pharmaceutical composition according to the present invention, lactose, dextrose, sucrose, oligosaccharides, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, and mineral oil may be used.

For formulation, commonly used diluents or excipients such as fillers, thickeners, binders, wetting agents, disintegrants, and surfactants are used.

The pharmaceutical composition according to the present invention is administered in a pharmaceutically effective amount. In the present invention, "the pharmaceutically effective amount" refers to an amount sufficient to treat diseases at a reasonable benefit/risk ratio applicable to medical treatment, and an effective dosage level may be determined according to factors including types of diseases of patients, the severity of disease, the activity of drugs, sensitivity to drugs, administration time, administration route, excretion rate, treatment period, and simultaneously used drugs, and factors well known in other medical fields.

The composition according to the present invention may be administered as an individual therapeutic agent or in combination with other therapeutic agents, may be administered sequentially or simultaneously with therapeutic agents in the related art, and may be administered in a single dose or multiple doses. It is important to administer the composition in a minimum amount that can obtain the maximum effect without any side effects, in consideration of all the aforementioned factors, and this may be easily determined by those of ordinary skill in the art.

The pharmaceutical composition of the present invention may be administered to a subject via various routes. All administration methods can be predicted, and the pharmaceutical composition may be administered via, for example, oral administration, subcutaneous injection, intraperitoneal injection, intravenous injection, intramuscular injection, intrathecal (space around the spinal cord) injection, sublingual administration, administration via the buccal mucosa, intrarectal insertion, intravaginal insertion, ocular administration, intra-aural administration, intranasal administration, inhalation, spraying via the mouth or nose, transdermal administration, percutaneous administration, or the like.

The pharmaceutical composition of the present invention is determined depending on the type of a drug, which is an active ingredient, along with various related factors such as a disease to be treated, administration route, the age, gender, and body weight of a patient, and the severity of diseases. Specifically, the effective amount of the composition according to the present invention may vary depending on the severity of the disease, the patient's age, sex, and body weight, and generally, 0.001 to 150 mg of the composition and preferably, 0.01 to 100 mg of the composition, per 1 kg of the body weight, may be administered daily or every other day or may be administered once to three times a day. However, since the effective amount may be increased or decreased depending on the administration route, the severity of obesity, gender, body weight, age, and the like, the dosage is not intended to limit the scope of the present invention in any way.

As used herein, the "subject" refers to a subject in need of treatment of a disease, and more specifically, refers to a mammal such as a human or a non-human primate, a mouse, a rat, a dog, a cat, a horse, and a cow, but the present invention is not limited thereto.

As used herein, the "administration" refers to providing a subject with a predetermined composition of the present invention by using an arbitrary appropriate method.

The term "prevention" as used herein means all actions that inhibit or delay the onset of a target disease. The term "treatment" as used herein means all actions that alleviate or beneficially change a target disease and abnormal metabolic symptoms caused thereby via administration of the pharmaceutical composition according to the present invention. The term "improvement" as used herein means all actions that reduce the degree of parameters related to a target disease, e.g., symptoms via administration of the composition according to the present invention.

The peptide or the complex according to the present invention may be used by adding the peptide or the complex as is to food or may be used together with other foods or food ingredients, but may be appropriately used according to a typical method. The mixed amount of the active ingredient may be suitably determined depending on the purpose of use thereof (for prevention or alleviation). In general, when a food or beverage is prepared, the peptide or the complex of the present invention is added in an amount of 15 wt % or less, preferably 10 wt % or less based on the raw materials. However, for long-term intake for the purpose of health and hygiene or for the purpose of health control, the amount may be less than the above-mentioned range, and the vesicles have no problem in terms of stability, so the active ingredient may be used in an amount more than the above-mentioned range.

The type of food is not particularly limited. Examples of food to which the material may be added include meats, sausage, bread, chocolate, candies, snacks, confectioneries, pizza, instant noodles, other noodles, gums, dairy products including ice creams, various soups, beverages, tea, drinks, alcoholic beverages, vitamin complexes, and the like, and include all health functional foods in a typical sense.

In addition to the aforementioned ingredients, the composition of the present invention may contain various nutrients, vitamins, electrolytes, flavors, colorants, pectic acids and salts thereof, alginic acid and salts thereof, organic acids, protective colloid thickeners, pH adjusters, stabilizers, preservatives, glycerin, alcohols, carbonating agents used in carbonated drinks, and the like. In addition, the composition of the present invention may contain flesh for preparing natural fruit juice, fruit juice drinks, and vegetable drinks. These ingredients may be used either alone or in combinations thereof. The proportion of these additives is not significantly important, but is generally selected within a range of 0.01 to 0.20 part by weight per 100 parts by weight of the composition of the present invention.

A formulation for the cosmetic composition according to the present invention may include a skin lotion, a skin softener, a skin toner, an astringent, a lotion, a milk lotion, a moisturizing lotion, a nourishing lotion, a massage cream, a nourishing cream, a mist, a moisturizing cream, a hand cream, a hand lotion, a foundation, an essence, a nourishing essence, a pack, soap, a cleansing foam, a cleansing lotion, a cleansing cream, a cleansing oil, a cleansing balm, a body lotion or a body cleanser.

A cosmetic composition of the present invention may further include a composition selected from the group consisting of water-soluble vitamins, oil-soluble vitamins, polymer peptides, polymeric polysaccharides, and sphingolipids.

The cosmetic composition of the present invention may include, as necessary, other ingredients mixed in conventional cosmetics along with the above essential ingredients.

Examples of additional ingredients to be mixed may include lipid components, a humectant, an emollient, a surfactant, organic and inorganic pigments, organic powder, a UV absorbent, a preservative, a sanitizer, an antioxidant, a plant extract, a pH adjuster, alcohol, pigments, flavors, a blood circulation promoter, a cooling agent, an anti-diaphoretic, and purified water.

Hereinafter, to help in understanding the present invention, exemplary examples will be suggested. However, it should be understood that the examples are not provided to limit the scope of the present invention and all alternatives and modifications within the scope of the accompanying claims are included in the present invention.

EXAMPLES

Example 1

Selection of Novel Cationic CPP 1-1. Process of Selecting Novel Cationic CPP

To select novel cationic cell penetrating peptides (cationic CPPs), all transcription factor protein sequences registered in NCBI were searched for, and a total of 1,224,223 protein sequences were obtained. To develop a method of selecting a novel cationic CPP from the obtained protein sequences, first, an experiment was conducted using Sus scrofa transcription factors to confirm the efficiency of the selected method.

A total number of the Sus scrofa transcription factors registered in NCBI was 3,253, and a total of 15,176 peptides were randomly extracted using a python script so that the amino acid length (window size) was 14 mer. From the extracted 14-mer peptides, peptides satisfying the following conditions were first selected: i) a peptide of 6.5 points or higher, as calculated when assigning 1 point for arginine (R) and 0.5 points for lysine (K), ii) a peptide including at least one proline (P), and iii) a peptide including at least one hydrophobic amino acid, such as valine (V), leucine (L), isoleucine (I), phenylalanine (F), and methionine (M).

Afterward, the cell penetration activity of the first-selected peptides was measured using the C3pred program (iGEM Tuebingen), and the top 1,000 peptides showing high cell penetration activity were secondarily selected.

Finally, the secondary structure of the secondarily selected peptides was predicted using the PEP2D (http://crdd.osdd.net/raghava/pep2d/) program, and a total of 145 peptides having an alpha helix structure were selected.

1-2. Synthesis of Novel Cationic CPP

Based on the selected 145 peptide sequences, the top 10 peptides predicted to exhibit high cell permeability were synthesized. The synthesis of the peptides was performed by coupling one by one from the C-terminus using a generally known Fmoc solid phase peptide synthesis (SPPS) method. In addition, in order to bind fluorescein isothiocyanate (FITC, iSpyBio) to each peptide as a representative example of a biologically active molecule, lysine (K) was added last during the peptide synthesis process, and FITC was bound to the free-amine residue of lysine. The FITC-bound peptides were purified by HPLC, and the molecular weight of the peptides was checked using a mass spectrometer, lyophilized, and stored frozen until use.

1-3. Confirmation of Characteristics of Novel Cationic CPP

To directly confirm the cell permeability of the 10 peptides produced according to the method of the above example, peptides were prepared at concentrations of 0.125, 0.25, 0.5, and 1 μM, respectively, and each peptide was treated in a HaCAT cell line, which is a human epidermal cell line. In further detail, HaCAT cells were seeded in 24-well plates to have a cell density of $1 \times 10^7$ cells/well, cultured in 10% fetal bovine serum (FBS)-added DMEM under conditions of 37° C. and 5% $CO_2$ for 24 hours, and then treated with each peptide and further incubated for one hour. As a control, FITC-conjugated TAT was used. After the culture was terminated, the cells were transferred to a sterile tube using 0.25% trypsin, and the medium was removed by centrifugation. Subsequently, the cells were washed with 500 μL of Dulbecco's phosphate-buffered saline (D-PBS) twice to completely remove the medium, and finally, resuspended using 400 μL of D-PBS, and intracellular fluorescence was measured by flow cytometry (FACS machine, BD Biosciences FACSCanto II).

As a result of intracellular fluorescence measurement, compared with the control TAT, peptides (Group 1) showing significantly high cell permeability in human epidermal cells are shown in Table 1, and peptides (Group 2) showing low cell permeability are shown in Table 2.

TABLE 1

Peptides having high cell permeability in human epidermal cells compared with TAT (SEQ ID NO: 61)

| CPP name | Sequence | SEQ ID NO: |
|---|---|---|
| C12 (Cat.12) | KPRKKKKRKNKKI | 4 |
| C14 (Cat.14) | ALVLLRRRRRDRKP | 8 |
| C16 (Cat.16) | RPRRKKQIKRLCKR | 7 |
| C31 (Cat.31) | IRAKKKKRRRKKKP | 13 |
| C52 (Cat.52) | TKRRKRRLRRRLTP | 9 |
| C67 (Cat.67) | KKRKKRRKKRKVDP | 2 |

TABLE 2

Peptides having low cell permeability in human epidermal cells compared with TAT (SEQ ID NO: 61)

| CPP | Sequence | SEQ ID NO: |
|---|---|---|
| C37 (Cat.37) | RALRRRAARAARRP | 58 |
| C45 (Cat.45) | ARKNRMARQRRLRP | 31 |
| C57 (Cat.57) | RRRQRKEKVRNQKP | 59 |
| C68 (Cat.68) | RALKLRRRRAVLP | 60 |

By comparatively analyzing the peptides of Groups 1 and 2, detailed differences between Groups 1 and 2 were confirmed. As a result, it was confirmed that peptide sequences having higher cell permeability in human epidermal cells compared with TAT have, in common, two amino acids selected from arginine (R) and lysine (K) at the $9^{th}$ and $10^{th}$ consecutive positions of the amino acid sequence, and one amino acid of lysine (K), threonine (T) and aspartate (D) are located at the $13^{th}$ amino acid. In addition, it was confirmed that two consecutive amino acids of KK, KL, or KR were located at the $5^{th}$ and $6^{th}$ amino acids.

Therefore, the CPP according to the present invention may be defined as follows:

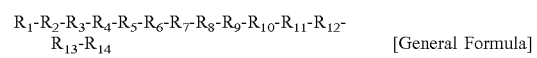

[General Formula]

(In General Formula, i) when calculated when arginine (R) is assigned 1 point, and lysine (K) is assigned 0.5 points, the total points of the peptide is 6.5 points or more;
    ii) one or more prolines (P) are included;
    iii) one or more amino acids selected from the group consisting of hydrophobic amino acids such as valine (V), leucine (L), isoleucine (I), phenylalanine (F), and methionine (M) are included;
    iv) all or a part has an alpha-helix structure; and/or
    v) has a positive charge as a cationic peptide.)

In addition, CPPs showing particularly high cell permeability in human epidermal cells may further satisfy the following characteristics:

(a) $R_5$-$R_6$ are any one set of consecutive amino acids selected from the group consisting of KK, KR, and LR;
(b) $R_9$ and $R_{10}$ are each independently arginine (R) or lysine (K); and/or
(c) $R_{13}$ is any one amino acid selected from the group consisting of lysine (K), threonine (T), and aspartate (D).

Example 2

Evaluation of Permeation Efficiency of Cationic CPP for Human Epidermal Cells and Neuroblastoma Cells 2-1. Evaluation of Cell Permeation Efficiency in Human Epidermal Cells The cell penetration efficiency of the cationic CPPs selected in Example 1 was evaluated using human epidermal cells. In further detail, HaCAT cells, which is a human epidermal cell line, were seeded in 24-well plates to have a cell density of $1 \times 10^7$ cells/well, and cultured in 10% FBS-added DMEM under conditions of 37° C. and 5% $CO_2$ for 24 hours. Subsequently, the cells were treated 4 μM each of the FITC-conjugated CPP or FITC-conjugated TAT, and incubated for one hour. After the termination of the incubation, the cells were transferred to a sterile tube using 0.25% trypsin, and the medium was removed through centrifugation. Afterward, the cells were washed with 500 μL of D-PBS twice to completely remove the medium, and finally, resuspended in 400 μL of D-PBS and intracellular fluorescence was measured by flow cytometry (FACSCanto II). The result is shown in FIG. 1.

As shown in FIG. 1, all of the CPPs according to the present invention (C12, C14, C16, C31, C52, and C67) exhibited increased cell permeability compared with TAT, which is conventionally known CPP, in human epidermal cells. Particularly, C16 exhibited 10-fold higher cell permeability compared with TAT.

2-2. Evaluation of Cell Penetration Efficiency in Human Neuroblastoma

The cell penetration efficiency of the cationic CPPs selected in Example 1 was evaluated in neuroblastoma. In further detail, SH-SYSY cells, which is a human neuroblastoma cell line, were seeded in 24-well plates to have a cell density of $1\times10^7$ cells/well, and cultured in 10% FBS-added DMEM under conditions of 37° C. and 5% $CO_2$ for 24 hours. In addition, the cells were treated with 4 μM each of FITC-conjugated CPPs (C12, C14, C16, C31, C52, and C67), or FITC-conjugated TAT, and incubated for one hour. After the termination of the incubation, the cells were transferred to a sterile tube using 0.25% trypsin and centrifuged to remove the medium. Afterward, the cells were washed with 500 μL of D-PBS twice to completely remove the medium, and finally, resuspended in 400 μL of D-PBS and intracellular fluorescence was measured by flow cytometry (FACSCanto II). The result is shown in FIG. 2.

Figure 2:
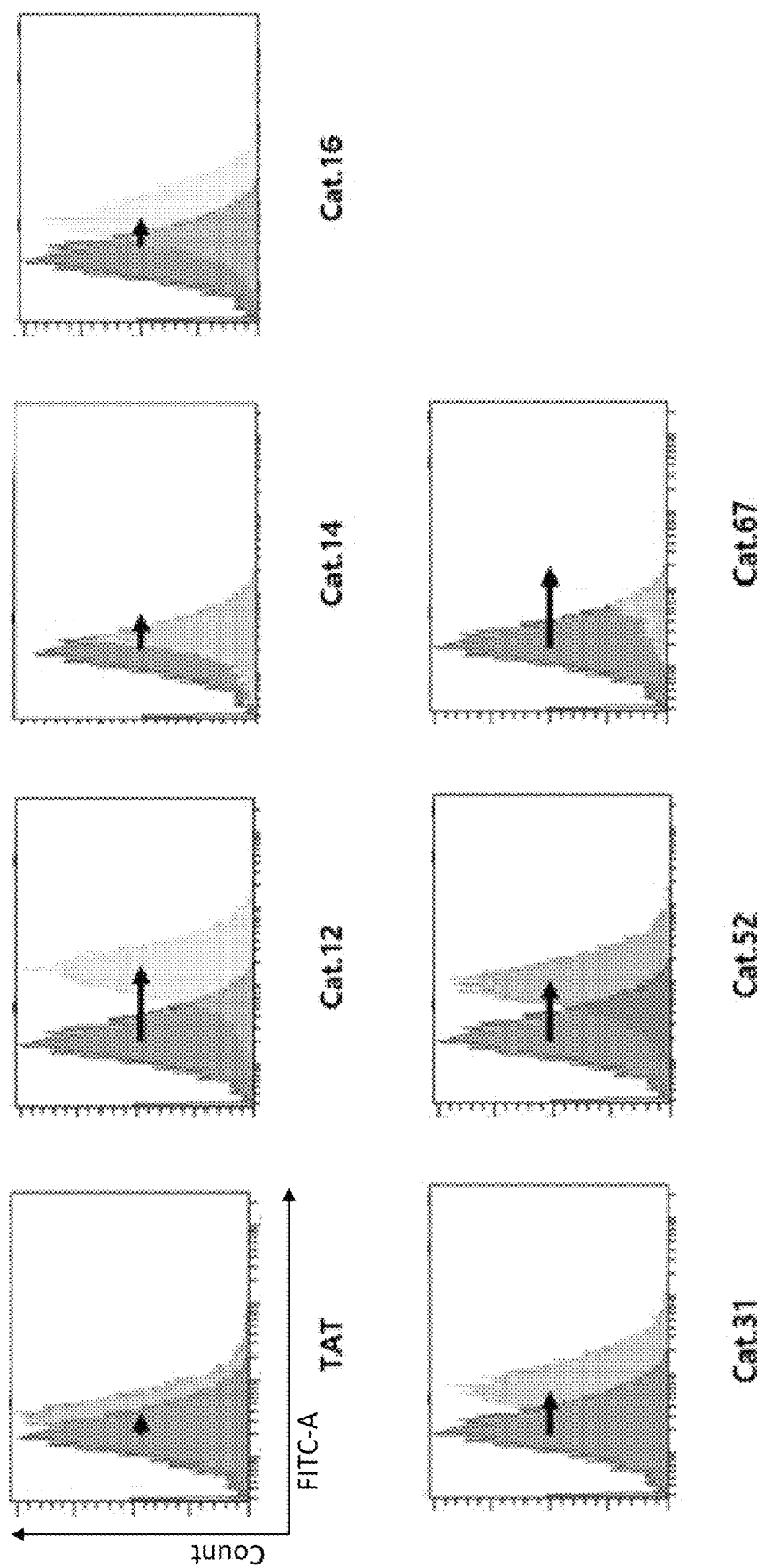
FIG. 2 shows a result of confirming the cell penetration efficiency of CPPs according to one embodiment of the present invention using a human neuroblastoma cell line.

As shown in FIG. 2, all of the CPPs showing high cell permeability in human epidermal cells showed significantly excellent cell permeability in human neuroblastoma, compared with TAT. Particularly, C12 showed 7-fold higher cell permeability, compared with TAT. That is, this means that CPP additionally satisfying the following characteristics as the CPP according to the present invention has high cell permeability and high biologically active material delivery capacity in not only human epidermal cells but human neuroblastoma cells or tissue:

(a) $R_5$-$R_6$ are any one set of consecutive amino acids selected from the group consisting of KK, KR, and LR;

(b) $R_9$ and $R_{10}$ are each independently arginine (R) or lysine (K); and/or (c) $R_{13}$ is any one amino acid selected from the group consisting of lysine (K), threonine (T), and aspartate (D).

Example 3

Confirmation of Intracellular Biologically Active Molecule Delivery Effect of Cationic CPP To confirm whether the cationic CPPs selected in Example 1 substantially deliver a biologically active molecule into cells, the location of the biologically active molecule was confirmed using a fluorescence microscope. In further detail, HaCAT cells or SH-SYSY cells were seeded on 24-well plates on which microscope cover glasses (12 mm Φ) were laid to have a cell density of $5\times10^4$ cells/well, and cultured in 10% FBS-added DMEM under conditions of 37° C. and 5% $CO_2$ for 18 hours to attach the cells onto the cover glasses. After the culture, the medium was removed, 500 μL of D-PBS and 300 μL of 4 μM CPP-added DMEM were added to the cells and incubated for one hour. After the completion of the incubation, to remove an extracellular protein, the cells were washed three times with 1 mL of D-PBS. The washed cells were fixed using 4% paraformaldehyde, and washed once again with 1 mL of D-PBS. The fixed cells were mounted using a mounting medium with aqueous DAPI, Fluoroshield (abcam), and observed using a fluorescence microscope. The result is shown in FIG. 3.

Figure 3:
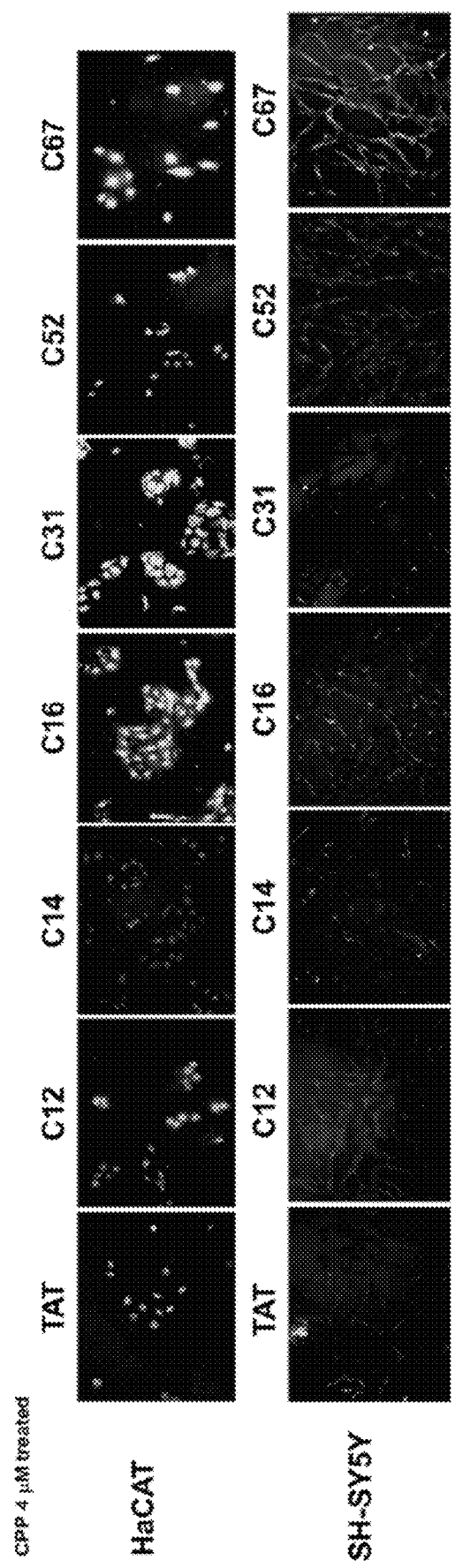
FIG. 3 shows a result of confirming whether CPPs according to the present invention deliver a biologically active molecule substantially attached to a peptide into cells using a fluorescence microscope.

As shown in FIG. 3, it was confirmed that the cationic CPPs according to the present invention effectively delivered a biological molecule bound to a peptide into cells by effectively penetrating human epidermal cells and human neuroblastoma cell through a cell membrane and the biological molecule delivery effect of the CPPs is much better than that of the conventional CPP (TAT). In addition, it was confirmed that the biological molecule delivered into cells by the CPP according to the present invention normally maintains inherent function and activity.

Example 4

Evaluation of Cell Penetration Efficiency in Neuroblastoma of Additionally Selected Peptides The present inventors deduced the common characteristic (amino acid sequence pattern) of novel cationic CPPs having significantly higher cell permeability than the related art through Example 1, and it was confirmed from Examples 2 and 3 that the CPPs show excellent cell permeability in human epidermal cells and neuroblastoma cells. Therefore, to confirm whether all of the peptides satisfying the amino acid sequence pattern exhibit high cell permeability, the top 50 peptides predicted to exhibit high cell permeability were additionally synthesized using the 145 peptide sequences selected in Example 1. Information on additionally synthesized peptides is shown in Table 3 below, and the sequence information of each peptide is disclosed in the sequence list of the specification.

TABLE 3

| CPP | Sequence | SEQ ID NO: |
|---|---|---|
| C72 | AARIRALRRRRRRP | 12 |
| C79 | MPKIRKLKRRKKFR | 13 |
| C82 | RLRALVRRKQRARP | 17 |
| C85 | LMPSKIRRRKKRKK | 18 |
| C93 | ARLRVILRRRNPKR | 7 |
| C95 | ARLRVILRRRHPRR | 8 |
| C102 | ARRLRRRTAKLPAR | 33 |
| C112 | IPLRRLMRRARRHR | 14 |
| C113 | WPRRRLRLRHRARR | 9 |
| C115 | KRKLKVRRKLREPR | 34 |
| C117 | RPALKQRRWRRKKK | 15 |
| C131 | RPIRKLLRQARQRR | 19 |
| C148 | AIKRRRRRALAKRP | 35 |
| C149 | AVKRRRRRALAKRP | 36 |
| C168 | RPIRKLVRKAREKR | 37 |
| C170 | RRALKRRAMRARRP | 38 |
| C179 | LVPRRLRRRARRRK | 10 |

TABLE 3-continued

| CPP | Sequence | SEQ ID NO: |
|---|---|---|
| C181 | RRALRRRAQRRGAP | 39 |
| C185 | SRRRLRRFLRRIAP | 11 |
| C190 | KARARRILRRRETP | 40 |
| C191 | KARARRILRRREAP | 41 |
| C201 | MKRLLKVVRRRRRP | 20 |
| C202 | RVAALLRRRRRERP | 21 |
| C203 | RRKVVREKRKRKLP | 42 |
| C208 | KRRKLRIKRRIRVP | 16 |
| C210 | RERKRAARKKIKKP | 57 |
| C214 | RKVLPRKQKRKRVK | 43 |
| C219 | RLRAIRRRRRSLDP | 44 |
| C223 | RTRLLRRLRALKPR | 22 |
| C226 | RPLVRRRLRRAVRR | 23 |
| C229 | ARVRARLRRRRIEP | 45 |
| C230 | YLRRKLRRRAGEPR | 24 |
| C236 | RVRAILRRTRRKEP | 25 |
| C262 | RLREKRRSLKRKRP | 46 |
| C264 | RLKEERLKKRRRSP | 58 |
| C282 | RVRALARRRRQARP | 26 |
| C283 | YRPRRKKITKKLKR | 27 |
| C284 | YRPRRKKATKKLKR | 28 |
| C310 | RERKRANRKKLKKP | 47 |
| C312 | LDRERRRKKAERRP | 59 |
| C319 | LRRVETLRRRKQPR | 48 |
| C341 | SVKRRRRRALAKRP | 49 |
| C354 | RIRALARRRDRRRP | 29 |
| C355 | RALRRRLHRQRKLP | 50 |
| C360 | RSPARKRVRAQKKR | 60 |
| C378 | RPRRKKQAKRLGKR | 30 |
| C379 | RPRRKKQVKRIGKR | 31 |
| C387 | RRREPLRARARVRR | 51 |
| C401 | RVRSLARRARRRTP | 52 |
| C402 | RVRTLLRRRRTERP | 32 |

Figure 4:
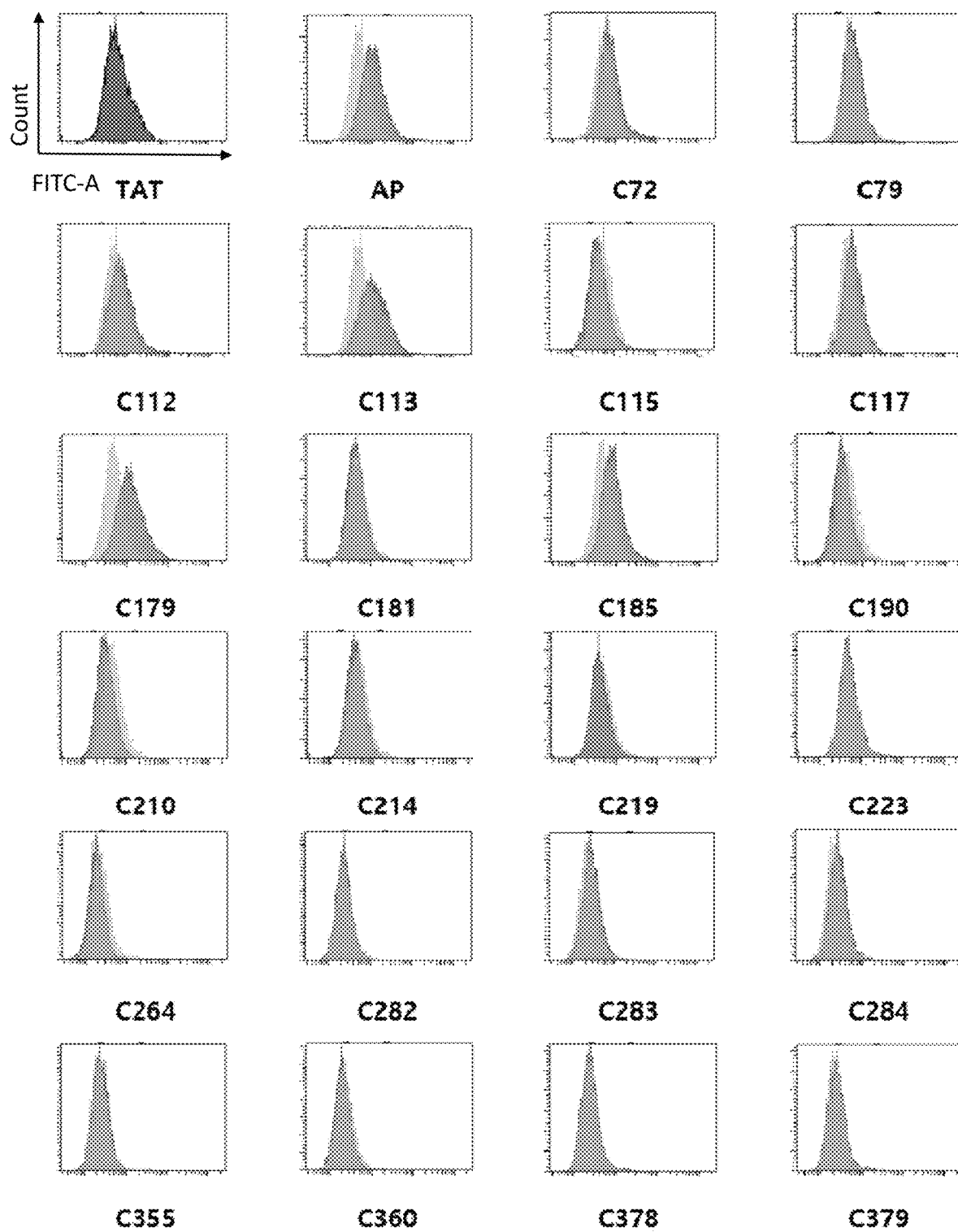
FIG. 4 shows a result of confirming the cell penetration efficiency of additionally selected CPPs using human epidermal cells.
Figure 5:
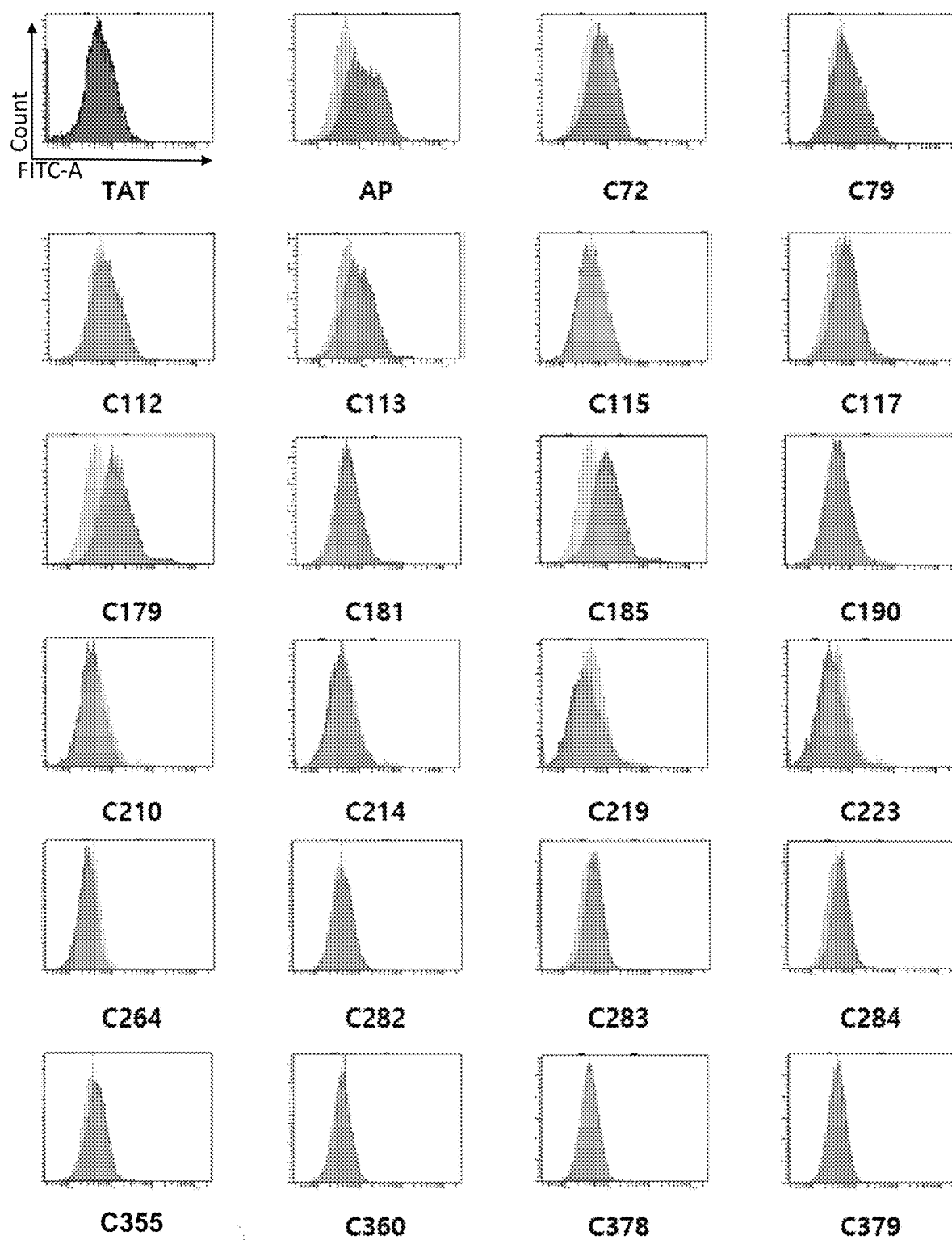
FIG. 5 shows a result of confirming the cell penetration efficiency of additionally selected CPPs using a human neuroblastoma cell line.
Figure 5:
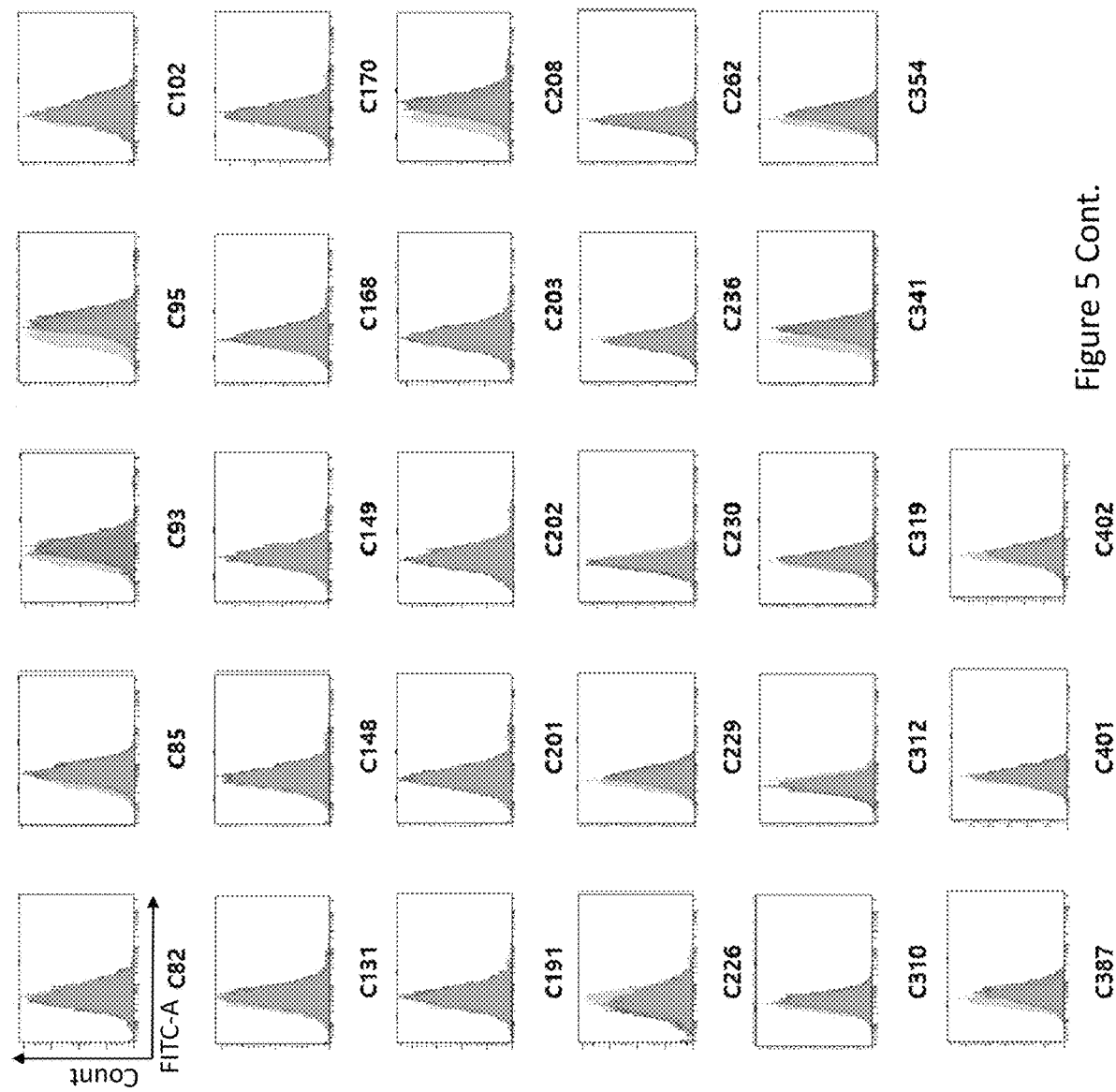

To evaluate the cell penetration efficiency of the additionally selected cationic CPPs, an experiment was conducted using human epidermal cells or human neuroblastoma cells. In further detail, HaCAT cells, which is a human epidermal cell line, or SH-SYSY cells, which is a human neuroblastoma cell line, were seeded in 24-well plates to have a cell density of $1 \times 10^7$ cells/well and cultured in 10% FBS-added DMEM under conditions of 37° C. and 5% $CO_2$ for 24 hours. In addition, the cells were treated with 4 μM each of FITC-conjugated peptides and FITC-conjugated TAT for one hour. After the completion of the culture, the cells were transferred to a sterile tube using 0.25% trypsin and centrifuged to remove the medium. Afterward, the cells were washed with 500 μL of D-PBS twice to completely remove the medium, and finally, resuspended in 400 μL of D-PBS and intracellular fluorescence was measured by flow cytometry (FACSCanto II). The result is shown in FIGS. 4 and 5.

Based on the result of the cell permeability of the CPPs confirmed in human neuroblastoma cells (SH-SYSY), the CPPs were divided into two groups: peptides having high cell permeability (Group 1) compared to the control TAT and peptides having low cell permeability (Group 2) compared to the control TAT in neuroblastoma. The results are shown in Tables 4 and 5.

TABLE 4

Peptides having high cell permeability in neuroblastoma compared with TAT (SEQ ID NO: 61)

| CPP | Score | Score/TAT | Sequence | SEQ ID NO: |
|---|---|---|---|---|
| C95 | 2417 | 4.657 | ARLRVILRRRHPRR | 8 |
| C67 | 2328 | 4.486 | KKRKKRRKKRKVDP | 6 |
| C179 | 2076 | 4.000 | LVPRRLRRRARRRK | 10 |
| C12 | 2062 | 3.973 | KPRKKKKRKNKKI | 1 |
| C93 | 1798 | 3.464 | ARLRVILRRRNPKR | 7 |
| C185 | 1684 | 3.245 | SRRRLRRFLRRIAP | 11 |
| C16 | 1680 | 3.237 | RPRRKKQIKRLCKR | 3 |
| C14 | 1382 | 2.663 | ALVLLRRRRRDRKP | 2 |
| C52 | 1328 | 2.559 | TKRRKRRLRRRLTP | 5 |
| C208 | 1326 | 2.555 | KRRKLRIKRRIRVP | 16 |
| C113 | 1278 | 2.462 | WPRRRLRLRHRARR | 9 |
| C72 | 1026 | 1.977 | AARIRALRRRRRRP | 12 |
| C31 | 998 | 1.923 | IRAKKKKRRRKKKP | 4 |
| C112 | 946 | 1.823 | IPLRRLMRRARRHR | 14 |
| C117 | 936 | 1.803 | RPALKQRRWRRKKK | 15 |
| C79 | 863 | 1.663 | MPKIRKLKRKKFR | 13 |
| C201 | 802 | 1.545 | MKRLLKVVRRRRRP | 20 |
| C85 | 798 | 1.538 | LMPSKIRRRKKRKK | 18 |
| C131 | 790 | 1.522 | RPIRKLLRQARQRR | 19 |
| C341 | 747 | 1.439 | SVKRRRRRALAKRP | 49 |
| C202 | 727 | 1.401 | RVAALLRRRRRERP | 21 |
| C102 | 720 | 1.387 | ARRLRRRTAKLPAR | 33 |
| C181 | 682 | 1.314 | RRALRRRAQRRGAP | 39 |
| C148 | 669 | 1.289 | AIKRRRRRALAKRP | 35 |
| C149 | 657 | 1.266 | AVKRRRRRALAKRP | 36 |
| C82 | 628 | 1.210 | RLRALVRRKQRARP | 17 |
| C168 | 608 | 1.171 | RPIRKLVRKAREKR | 37 |

TABLE 4-continued

Peptides having high cell permeability
in neuroblastoma compared with TAT
(SEQ ID NO: 61)

| CPP | Score | Score/TAT | Sequence | SEQ ID NO: |
|---|---|---|---|---|
| C170 | 605 | 1.166 | RRALKRRAMRARRP | 38 |
| C191 | 592 | 1.141 | KARARRILRRREAP | 41 |
| C190 | 579 | 1.116 | KARARRILRRRETP | 40 |
| C45 | 570 | 1.098 | ARKNRMARQRRLRP | 53 |
| C354 | 564 | 1.087 | RIRALARRRDRRRP | 29 |
| C115 | 563 | 1.085 | KRKLKVRRKLREPR | 34 |
| C387 | 560 | 1.079 | RRREPLRARARVRR | 51 |
| C203 | 544 | 1.048 | RRKVVREKRKRKLP | 42 |
| C229 | 536 | 1.033 | ARVRARLRRRRIEP | 45 |
| C284 | 532 | 1.025 | YRPRRKKATKKLKR | 28 |

TABLE 5

Peptides having low cell permeability in
neuroblastoma compared with TAT (SEQ ID NO: 61)

| CPP | Score | Score/TAT | Sequence | SEQ ID NO: |
|---|---|---|---|---|
| C283 | 514 | 0.990 | YRPRRKKITKKLKR | 27 |
| C355 | 497 | 0.958 | RALRRRLHRQRKLP | 50 |
| C226 | 474 | 0.913 | RPLVRRRLRRAVRR | 23 |
| C214 | 459 | 0.884 | RKVLPRKQKRKRVK | 43 |
| C219 | 453 | 0.873 | RLRAIRRRRRSLDP | 44 |
| C310 | 452 | 0.871 | RERKRANRKKLKKP | 47 |
| C282 | 441 | 0.850 | RVRALARRRRQARP | 26 |
| C402 | 437 | 0.842 | RVRTLLRRRRTERP | 32 |
| C319 | 436 | 0.840 | LRRVETLRRRKQPR | 48 |
| C401 | 425 | 0.819 | RVRSLARRARRRTP | 52 |
| C223 | 408 | 0.786 | RTRLLRRLRALKPR | 22 |
| C378 | 400 | 0.771 | RPRRKKQAKRLGKR | 30 |
| C236 | 395 | 0.761 | RVRAILRRTRRKEP | 25 |
| C379 | 391 | 0.753 | RPRRKKQVKRIGKR | 31 |
| C360 | 388 | 0.748 | RSPARKRVRAQKKR | 60 |
| C210 | 386 | 0.744 | RERKRAARKKIKKP | 57 |
| C262 | 345 | 0.665 | RLREKRRSLKRKRP | 46 |
| C230 | 305 | 0.588 | YLRRKLRRRAGEPR | 24 |
| C312 | 271 | 0.522 | LDRERRRKKAERRP | 59 |
| C264 | 268 | 0.516 | RLKEERLKKRRRSP | 58 |
| C37 | 0 | 0.000 | RALRRRAARAARRP | 54 |

TABLE 5-continued

Peptides having low cell permeability in
neuroblastoma compared with TAT (SEQ ID NO: 61)

| CPP | Score | Score/TAT | Sequence | SEQ ID NO: |
|---|---|---|---|---|
| C57 | 0 | 0.000 | RRRQRKEKVRNQKP | 55 |
| C68 | 0 | 0.000 | RALKLRRRRAVLP | 56 |

As shown in the above tables, CPP consisting of any one amino acid sequence of SEQ ID NOs: 1 to 21, 28, 29, 33 to 42, 45, 49, 51, and 53 has higher cell permeability in neuroblastoma compared with the conventional CPP, which is TAT, and particularly, the CPP consisting of any one amino acid sequence of SEQ ID NOs: 1 to 21, 28, 29, 33 to 42, 45, 49, 51, and 53 exhibits approximately 2-fold or higher cell permeability than TAT.

In addition, as a result of analyzing the characteristics of CPPs (SEQ ID NO: 1 to 21, 28, 29, 33 to 42, 45, 49, 51, and 53) having high cell permeability compared with TAT, it was confirmed that the CPPs can be defined as a peptide of the following General Formula:

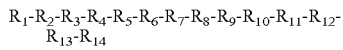  [General Formula]

(In General Formula, $R_{14}$ is arginine (R), proline (P), lysine (K), or isoleucine (I);

at least one of $R_1$ to $R_{14}$ is proline (P);

when arginine (R) is assigned 1 point and lysine (K) is assigned 0.5 points among $R_1$ to $R_{14}$, the sum of the peptide is 6.5 points or more; and the peptide includes one or more amino acids selected from the group consisting of valine (V), leucine (L), and isoleucine (I).)

Particularly, as a result of analyzing the characteristics of CPPs having an exceptionally high cell permeability, compared with TAT, in neuroblastoma and epidermal cells (SEQ ID NOs: 1 to 11), the CPPs further satisfy the following characteristics:

i) In General Formula, $R_5$-$R_6$ is any one set of consecutive amino acids selected from the group consisting of VI, KR, RL, KK, LR, and RA;

ii) $R_9$ and $R_{10}$ are each independently arginine (R), lysine (K), alanine (A), leucine (L), or histidine (H);

iii) $R_{13}$ is arginine (R), aspartic acid (D), lysine (K), alanine (A), threonine (T), or valine (V);

iv) $R_2$ is proline (P), leucine (L), arginine (R), lysine (K), valine (V), or alanine (A); and/or v) the peptide does not include glutamic acid (E), glycine (G), methionine (M), and tyrosine (Y).

Example 5

Confirmation of Biologically Active Molecule Delivery Effect of Cationic CPPs Per Cell and Tissue Subsequently, to confirm whether the CPPs according to the present invention show excellent cell permeability into different types of cells/tissues, various tissue-derived cells were treated with biologically active molecule-conjugated CPPs to compare its delivery capacity with TAT. As in the previous examples, each cell was aliquoted in a plate at an appropriate density, and cultured in a 10% FBS-added medium under a condition of 37° C. and 5% $CO_2$ for 24 hours. Subsequently, the cells were treated with 4 μM each of FITC-conjugated CPP or FITC-conjugated TAT and incubated for one hour. After the completion of the incubation, the cells were transferred to a sterile tube using 0.25% trypsin and centrifuged to remove the medium. Afterward, the cells were washed with 500 μL of D-PBS twice to completely remove the medium, and finally, resuspended in 400 μL of D-PBS and intracellular fluorescence was measured by flow cytometry (FACSCanto II).

Macrophages were used by inducing differentiation from THP1 cells. Specifically, the THP-1 cells were aliquoted on a cover glass laid on a 24-well plate to have a density of $6 \times 10^4$ cells/well, and after the addition of 100 ng/mL of phorbol 12-myristate 13-acetate (PMA), the cells were incubated for 48 hours to induce the differentiation into macrophages. After 48 hours, the cells were washed with Dulbecco's phosphate buffered saline (DPBS) to perform an experiment.

5-1. Evaluation of Cell Penetration Efficiency Using Macrophages

Figure 6:
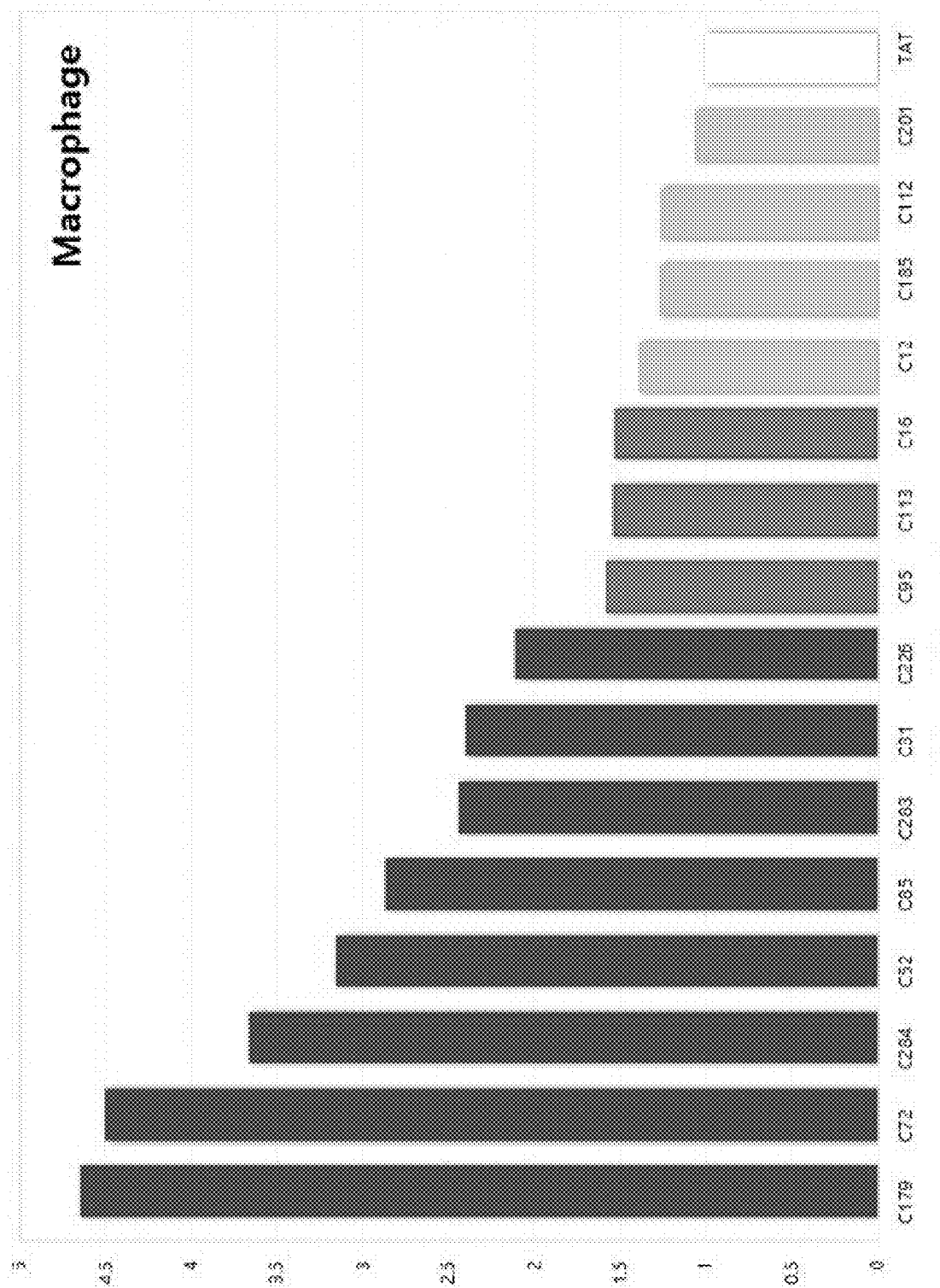
FIG. 6 shows a graph of comparing the cell permeability of CPP and TAT according to the present invention in macrophages.

The cell permeability of the CPP according to the present invention into macrophages is shown in FIG. 6. Compared with the convention CPP, which is TAT, C179, C72, C284, C52, C85, C283, C31, C226, C95, C113, C16, C12, C185, C112, and C201 exhibited higher cell permeability into macrophages, and particularly, C179, C72, C284, C52, C85, C283, C31, and C226 exhibited 2-fold higher cell permeability than TAT, confirming that they are particularly suitable CPPs for the delivery of a biologically active material into macrophages.

5-2. Evaluation of Cell Penetration Efficiency Using Monocytes

Figure 7:
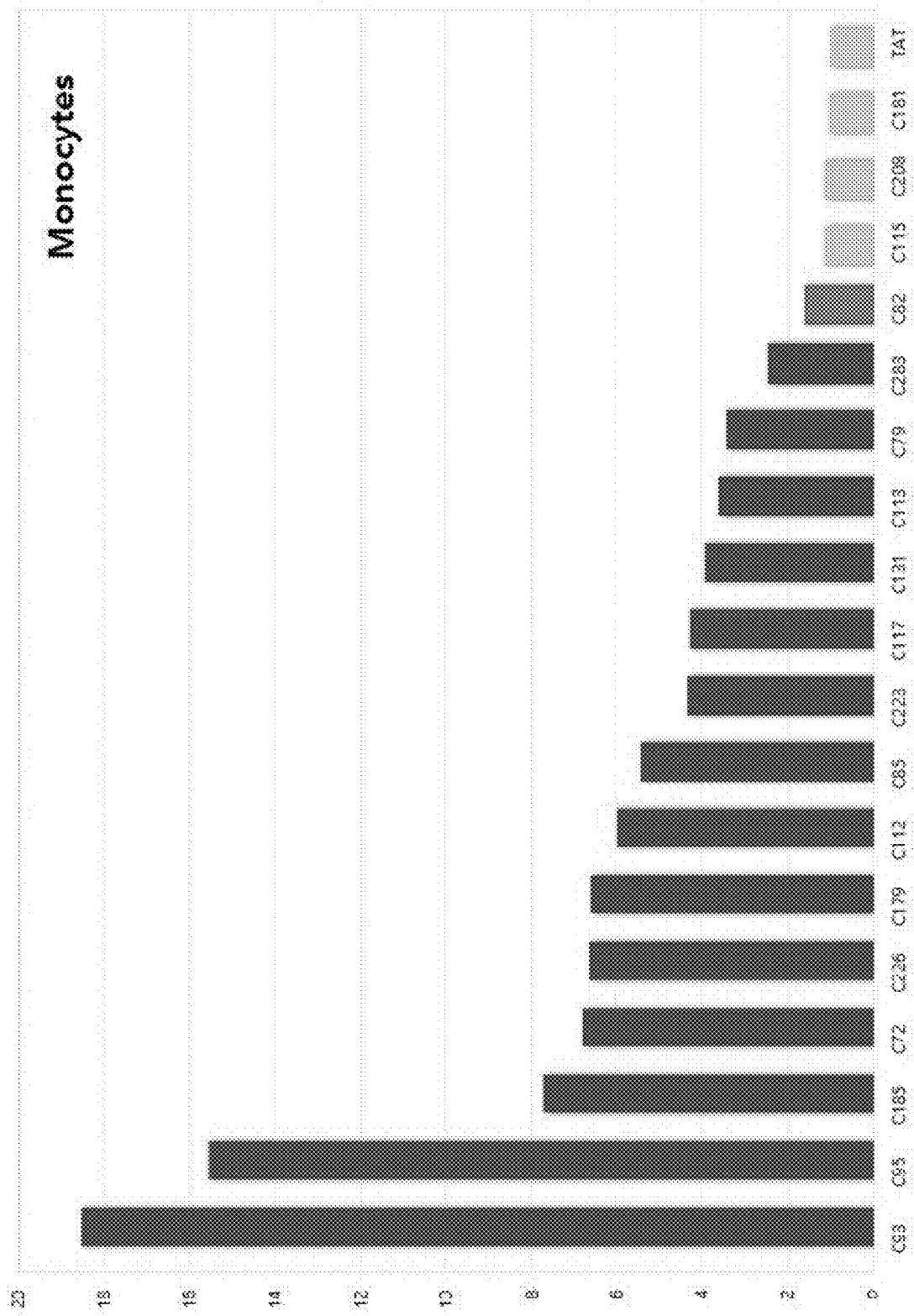
FIG. 7 shows a graph of comparing the cell permeability of CPP and TAT according to the present invention in monocytes.

The cell permeability of the CPP according to the present invention into monocytes is shown in FIG. 7. Compared with conventional CPP, which is TAT, C93, C95, C185, C72, C226, C179, C112, C85, C223, C117, C131, C113, C79, C283, C82, C115, C208, and C181 exhibited higher cell permeability into monocytes, and particularly, C93, C95, C185, C72, C226, C179, C112, C85, C223, C117, C131, C113, C79, and C283 exhibited 2-fold higher cell permeability than TAT, confirming that they are particularly suitable CPPs for the delivery of a biologically active material into monocytes.

5-3. Evaluation of Cell Penetration Efficiency Using Brain Cells

Figure 8:
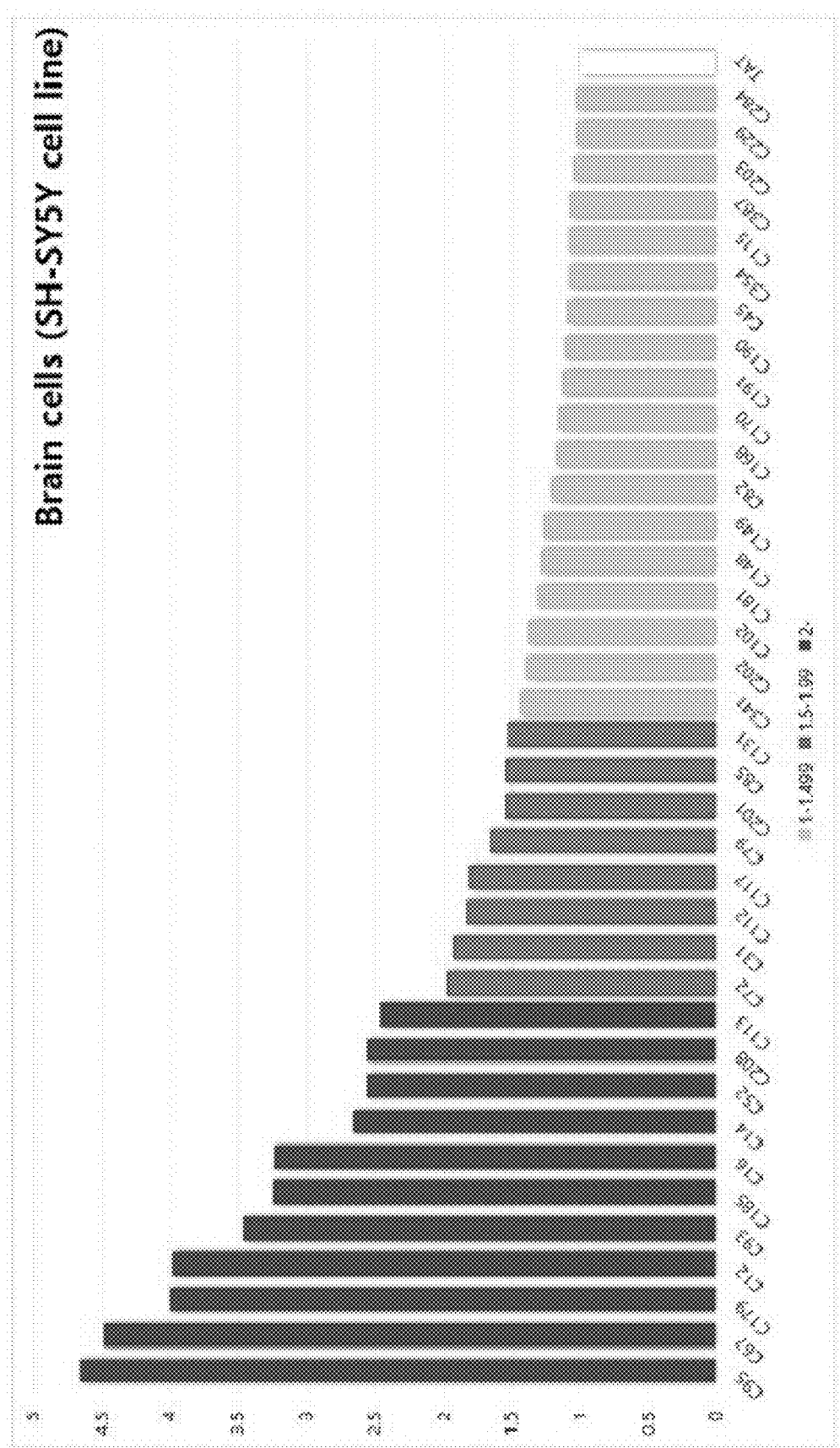
FIG. 8 shows a graph of comparing the cell permeability of CPP and TAT according to the present invention in brain cells (SH-SY5Y cells)

The cell permeability of the CPP according to the present invention into neuroblastoma cells (SH-SY5Y cell line) was confirmed again, and the result is shown in FIG. 8. Compared with the conventional CPP, which is TAT, C95, C67, C179, C12, C93, C185, C16, C14, C52, C208, C113, C72, C31, C112, C117, C79, C201, C85, C131, C341, C202, C102, C181, C148, C149, C82, C168, C170, C191, C190, C45, C354, C115, C387, C203, C229, and C284 exhibited higher cell permeability in bran cells, and particularly, C95, C67, C179, C12, C93, C185, C16, C14, C52, C208, and C113 exhibited 2-fold higher cell permeability than TAT, confirming that they are particularly suitable CPPs for the delivery of a biologically active material into brain cells.

Figure 9:
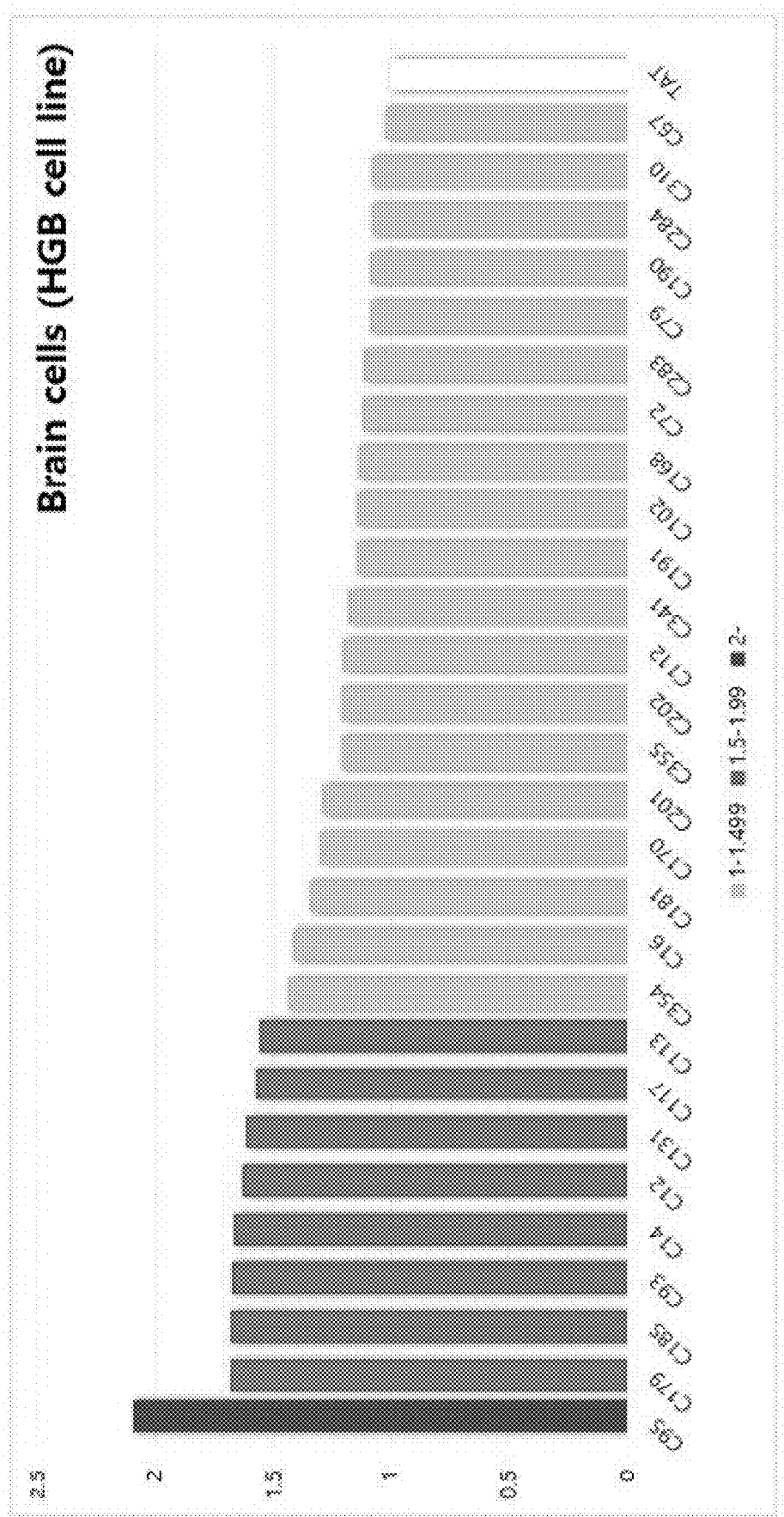
FIG. 9 shows a graph of comparing the cell permeability of CPP and TAT according to the present invention in other brain cells (HGB cells)

The cell permeability for another human glioblastoma cell (HGB cell line) is shown in FIG. 9. Compared with the conventional CPP, which is TAT, C95, C179, C185, C93, C14, C12, C131, C117, C113, C354, C16, C181, C170, C201, C355, C202, C112, C341, C191, C102, C168, C72, C283, C79, C190, C284, C310, and C67 exhibited higher cell permeability in brain cells, and particularly, C95 exhibited 2-fold higher cell permeability than TAT, confirming that it is a particularly suitable CPP for the delivery of a biologically active material into brain cells or brain tissue.

5-4. Evaluation of Cell Penetration Efficiency Using Skin Cells

Figure 10A:
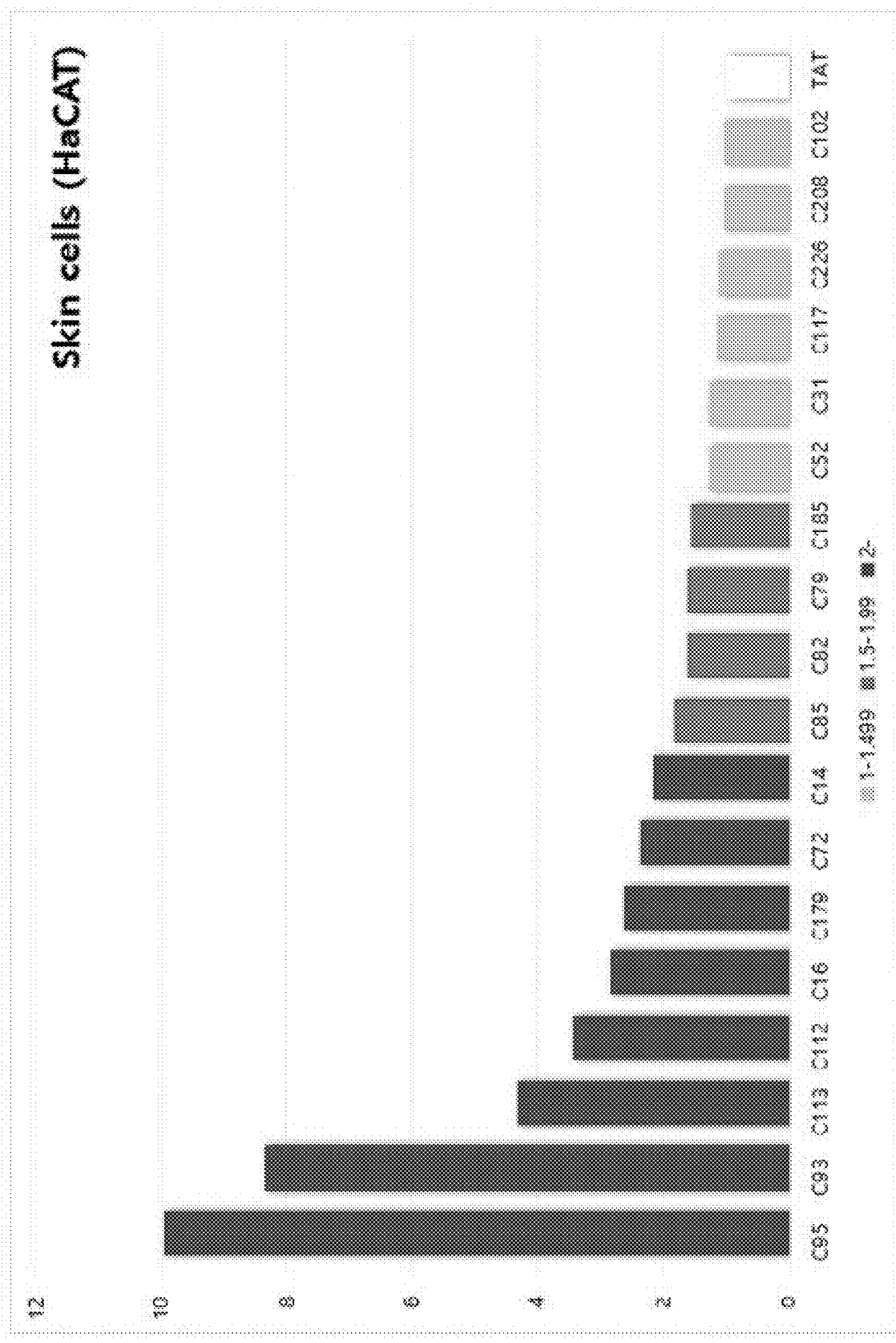
FIG. 10A shows a graph of comparing the cell permeability of CPP and TAT according to the present invention in skin cells (HaCAT cells)
Figure 10B:
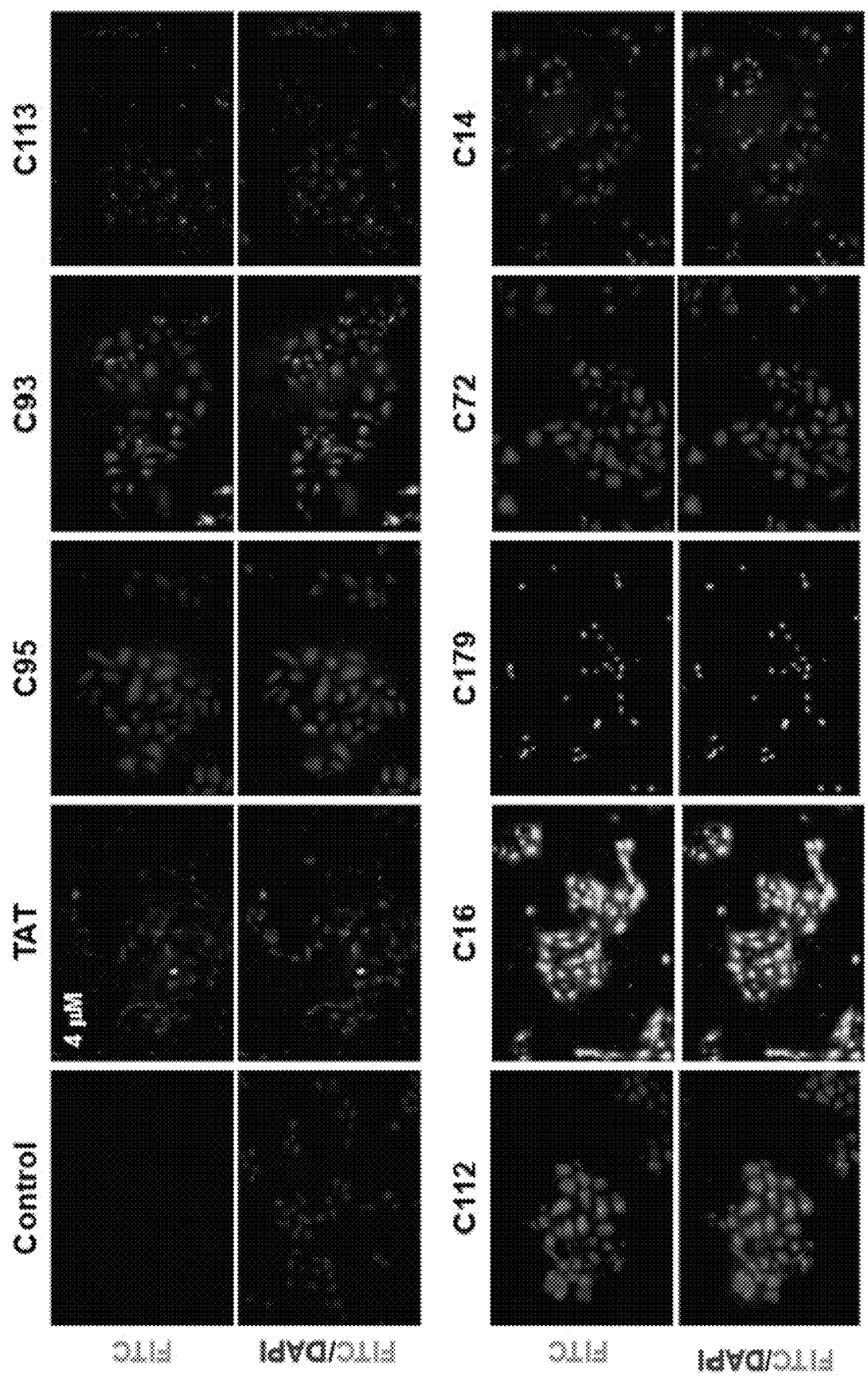
FIG. 10B shows a fluorescence microscopic photograph of CPPs showing high cell permeability particularly in skin cells.

The cell permeability of the CPP according to the present invention into skin cells (HaCAT cell line) is shown in FIG. 10A. Compared with the conventional CPP, which is TAT, C95, C93, C113, C112, C16, C179, C72, C14, C85, C82, C79, C185, C52, C31, C117, C226, C208, and C102 exhibited higher cell permeability in skin cells, and particularly, C95, C93, C113, C112, C16, C179, C72, and C14 exhibited 2-fold higher cell permeability than TAT, confirming that they are particularly suitable CPPs for the delivery of a biologically active material into skin cells or skin tissue. The CPPs showing 2-fold higher cell permeability than TAT in skin cells were photographed using a fluorescence microscope, and the photographs are shown in FIG. 10B.

Figure 11:
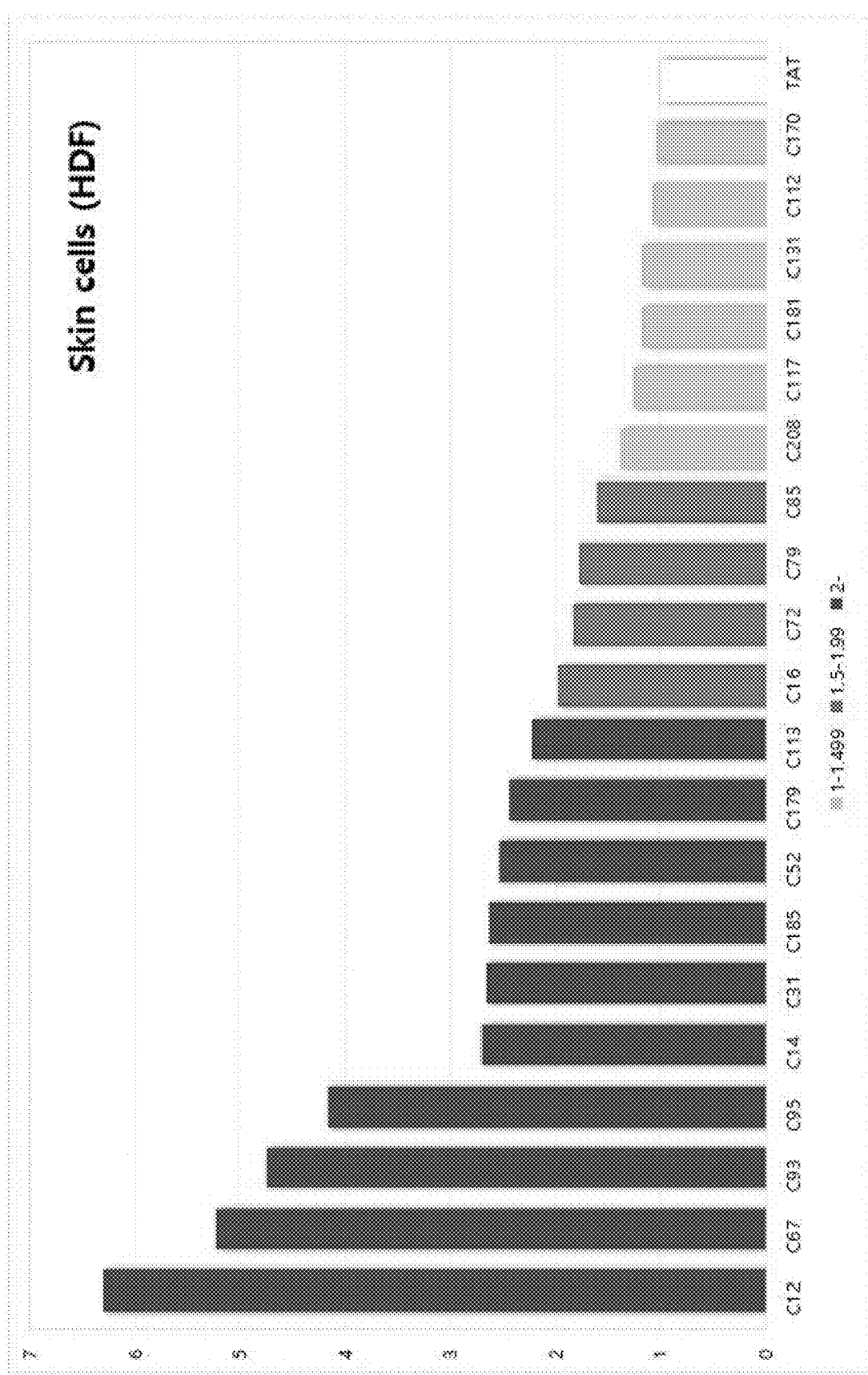
FIG. 11 shows a graph of comparing the cell permeability of CPP and TAT according to the present invention in other skin cells (HDF cells)

The cell permeability for another skin cell (HDF cell line) is shown in FIG. 11. Compared with the conventional CPP, which is TAT, C12, C67, C93, C95, C14, C31, C185, C52, C179, C113, C16, C72, C79, C85, C208, C117, C181, C131, C112, and C170 exhibited higher cell permeability in skin cells, and particularly, C12, C67, C93, C95, C14, C31, C185, C52, C179, and C113, compared with TAT, exhibited 2-fold higher cell permeability confirming that they are particularly suitable CPPs for the delivery of a biologically active material into skin cells or skin tissue.

5-5. Evaluation of Cell Penetration Efficiency Using Cervical Cancer Cells

Figure 12:
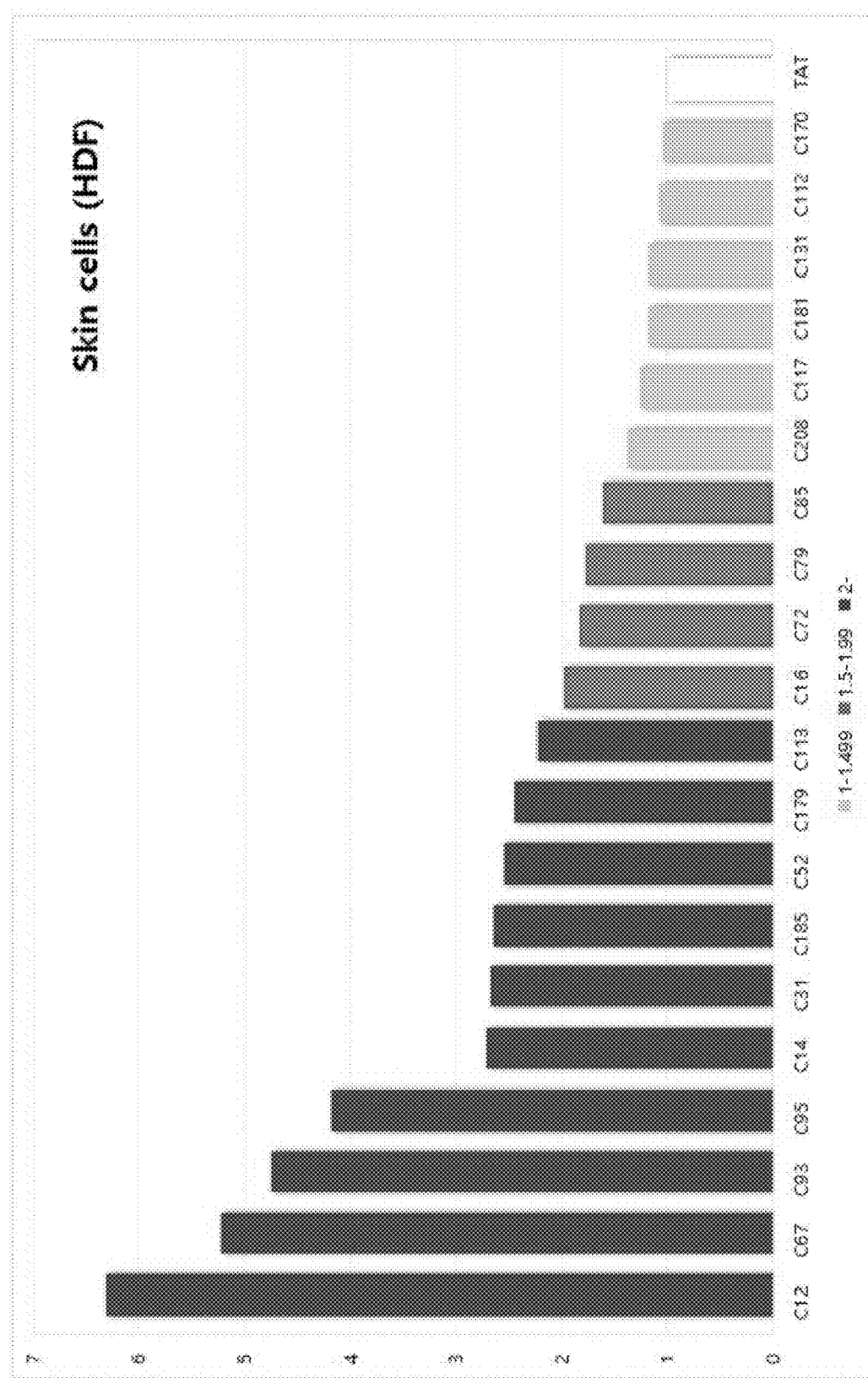
FIG. 12 shows a graph of comparing the cell permeability of CPP and TAT according to the present invention in cervical cancer cells (HaLa)

The cell permeability of the CPP according to the present invention in cervical cancer cells (HeLa cell line) is shown in FIG. 12. Compared with the conventional CPP, which is TAT, C16, C113, C179, C31, C208, C14, C67, C226, C185, C201, C283, C52, C12, C223, C379, C236, C230, C378, C219, C202, C117, C354, C229, C214, C341, C191, C112, C387, C72, C148, C131, C319, C262, C79, C282, C93, C203, C181, C284, C355, and C170 exhibited higher cell permeability in cervical cancer cells, and particularly, C16, C113, C179, C31, C208, C14, C67, C226, C185, C201, C283, and C52 exhibited 2-fold higher cell permeability than TAT, confirming that they are particularly suitable CPPs for the delivery of a biologically active material in cervical tumor tissue into cervical cancer cells.

5-6. Evaluation of Cell Penetration Efficiency Using Connective Tissue Cells

Figure 13A:
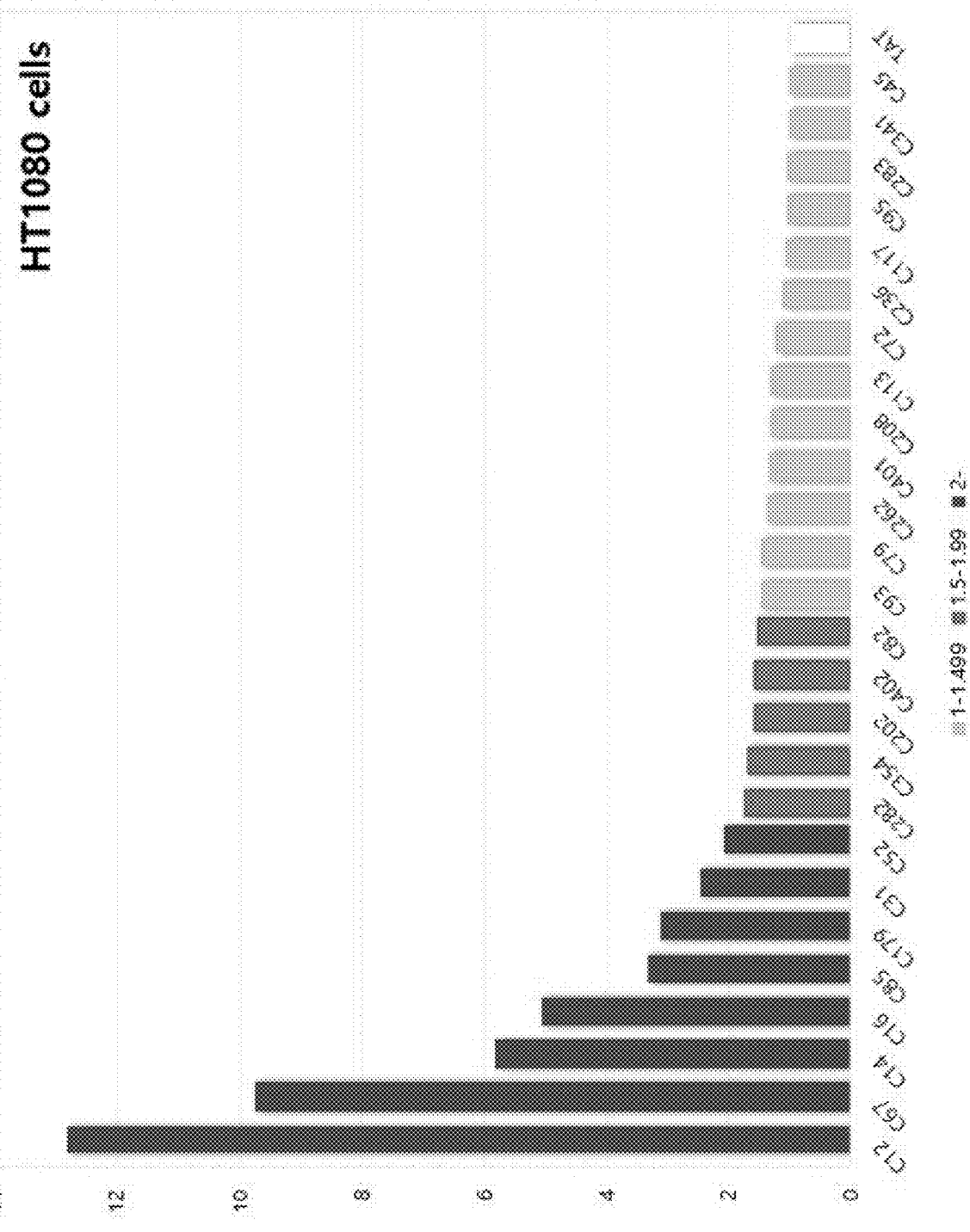
FIG. 13A shows a graph of comparing the cell permeability of CPP and TAT according to the present invention in connective tissue cells (HT1080 cells)
Figure 13B:
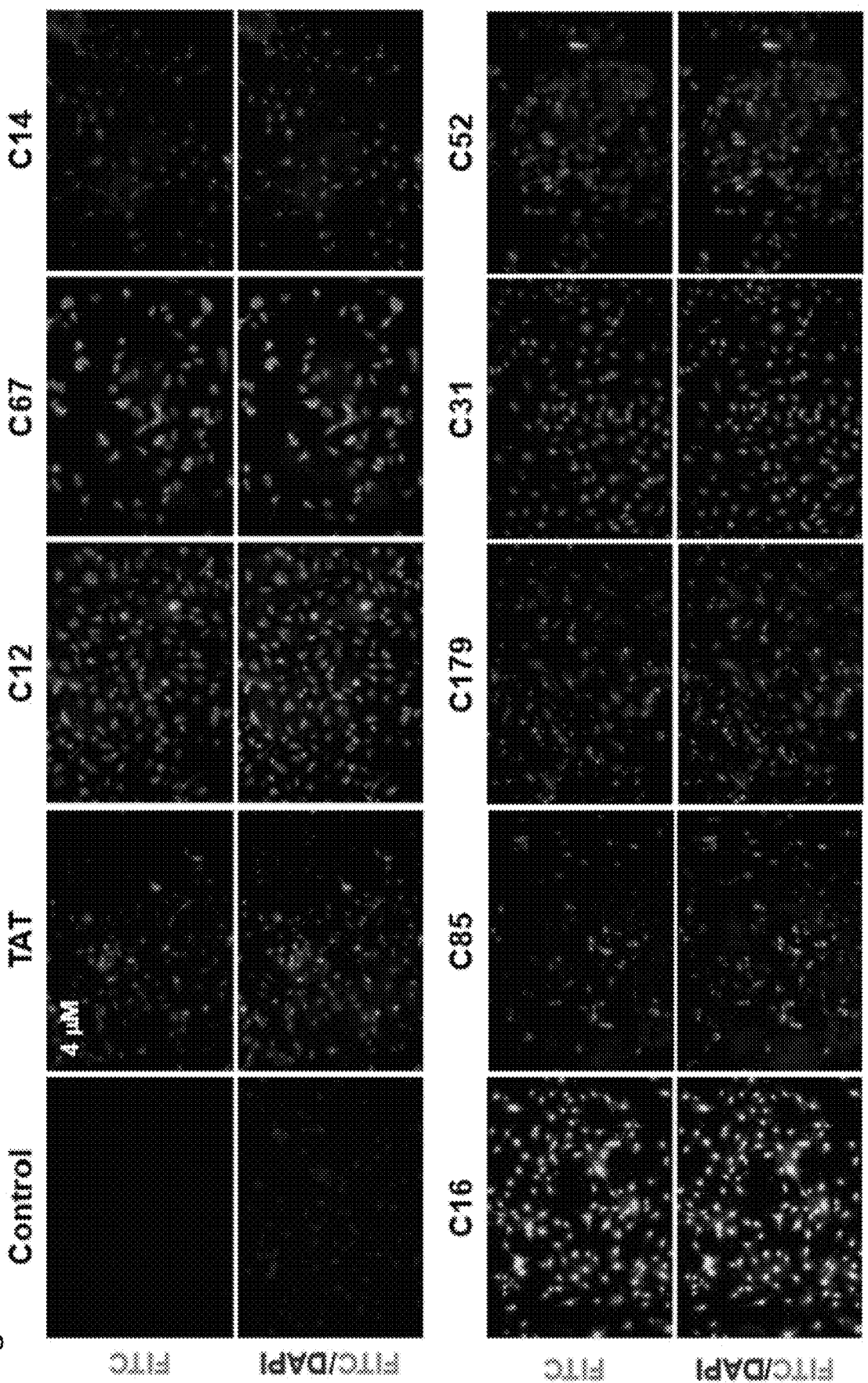
FIG. 13B is a fluorescence microscopic photograph of CPPs showing high cell permeability particularly in connective tissue cells.

The cell permeability of the CPP according to the present invention for fibrosarcoma cells (HT1080 cell line; specifically, connective tissue cells) is shown in FIG. 13A. Compared with the conventional CPP, which is TAT, C12, C67, C14, C16, C85, C179, C31, C52, C282, C354, C202, C402, C82, C93, C79, C262, C401, C208, C113, C72, C236, C117, C95, C283, C341, and C45 exhibited higher cell permeability in fibrosarcoma cells, and particularly, C12, C67, C14, C16, C85, C179, C31, and C52 exhibited 2-fold higher cell permeability than TAT, confirming that they are particularly suitable CPPs for the delivery of a biologically active material into connective tissue cells or various connective tissues. The CPPs showing 2-fold higher cell permeability than TAT in connective tissue cells were photographed using a fluorescence microscope, and the photographs are shown in FIG. 13B.

5-7. Evaluation of Cell Penetration Efficiency Using Liver Cells

Figure 14A:
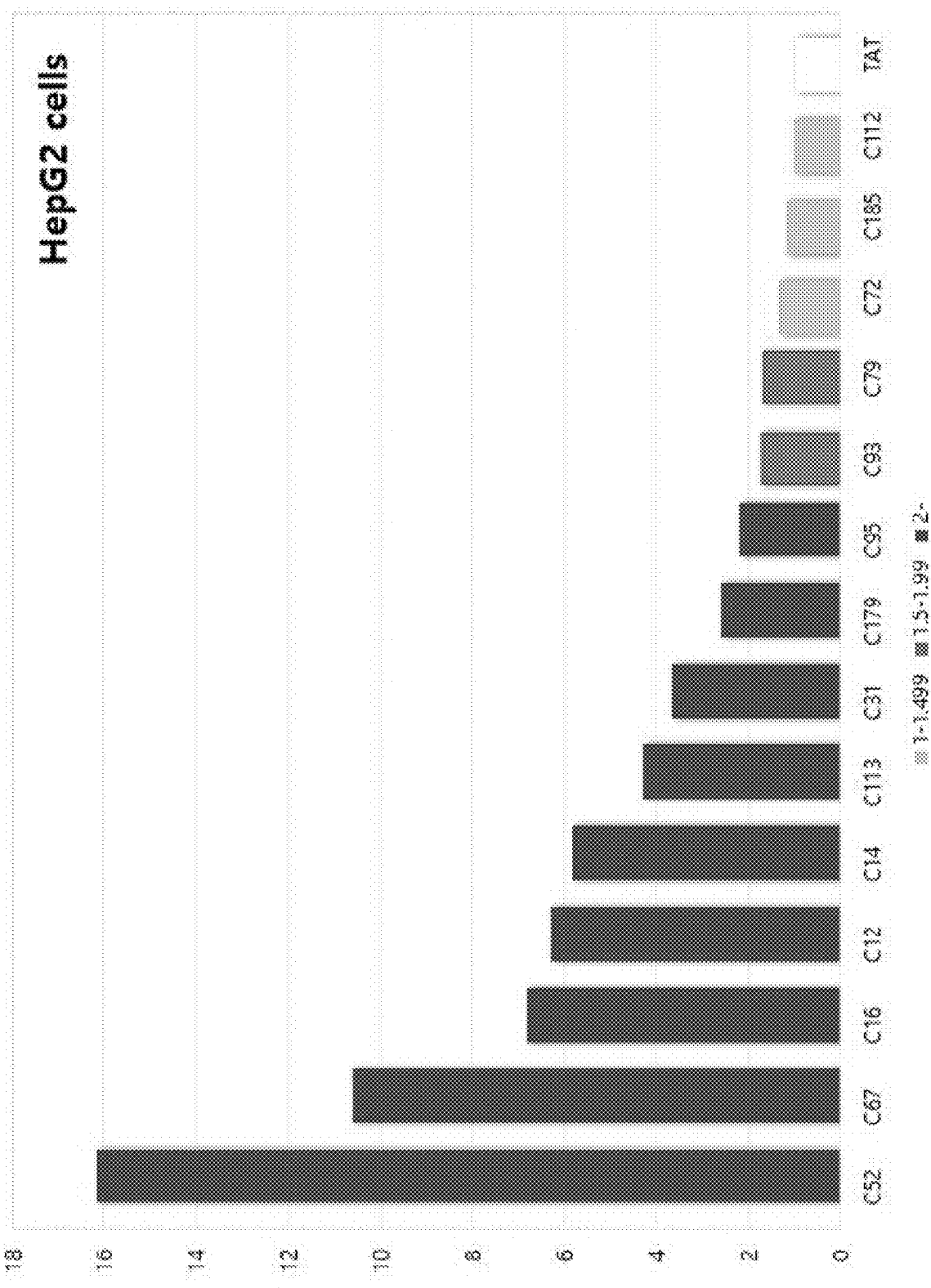
FIG. 14A is a graph of comparing the cell permeability of CPP and TAT according to the present invention in liver cells (HepG2 cells)
Figure 14B:
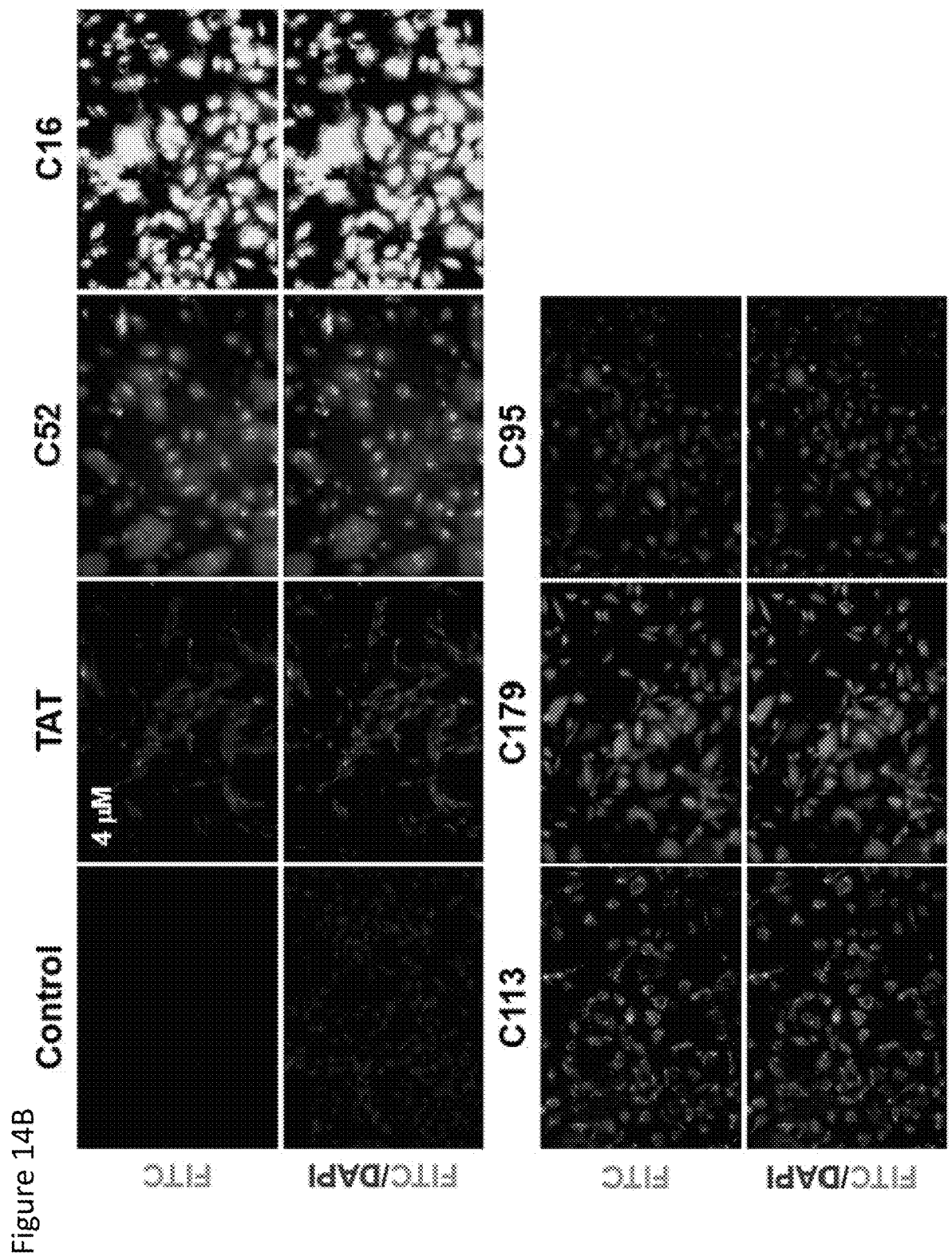
FIG. 14B is a fluorescence microscopic photograph of CPPs showing high cell permeability particularly in liver cells.

The cell permeability of the CPP according to the present invention for liver cells (HepG2 cell line) is shown in FIG. 14A. Compared with the conventional CPP, which is TAT, C52, C67, C16, C12, C14, C113, C31, C179, C95, C93, C79, C72, C185, and C112 exhibited higher cell permeability in liver cells, and particularly, C52, C67, C16, C12, C14, C113, C31, C179, and C95 exhibited 2-fold higher cell permeability than TAT, confirming that they are particularly suitable CPPs for the delivery of a biologically active material into liver cells or liver tissue. The CPPs showing 2-fold higher cell permeability than TAT in liver cells were photographed using a fluorescence microscope, and the photographs are shown in FIG. 14B.

5-8. Evaluation of Cell Penetration Efficiency Using Kidney Cells

Figure 15:
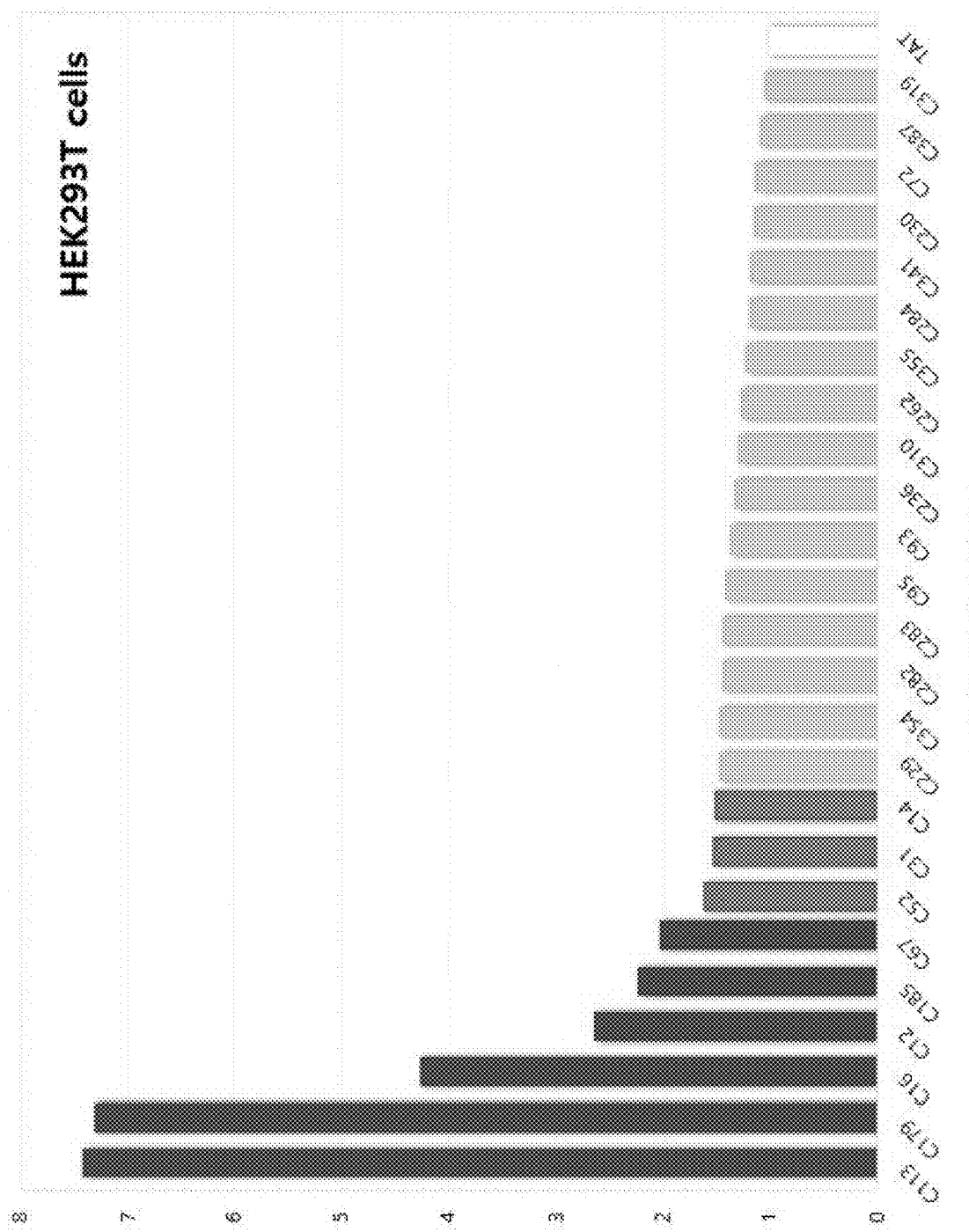
FIG. 15 is a graph of comparing CPP and TAT according to the present invention in kidney cells (HEK293T cells)

The cell permeability of the CPP according to the present invention for kidney cells (HEK293T cell line) is shown in FIG. 15. Compared with the conventional CPP, which is TAT, C113, C179, C16, C12, C185, C67, C52, C31, C14, C229, C354, C282, C283, C95, C93, C236, C310, C262, C355, C284, C341, C230, C72, C387, and C319 exhibited higher cell permeability in kidney cells, and particularly, C113, C179, C16, C12, C185, and C67 exhibited 2-fold higher cell permeability than TAT, confirming that they are particularly suitable CPPs for the delivery of a biologically active material into kidney cells or kidney tissue.

5-9. Evaluation of Cell Penetration Efficiency Using Lung Cells

Figure 16:
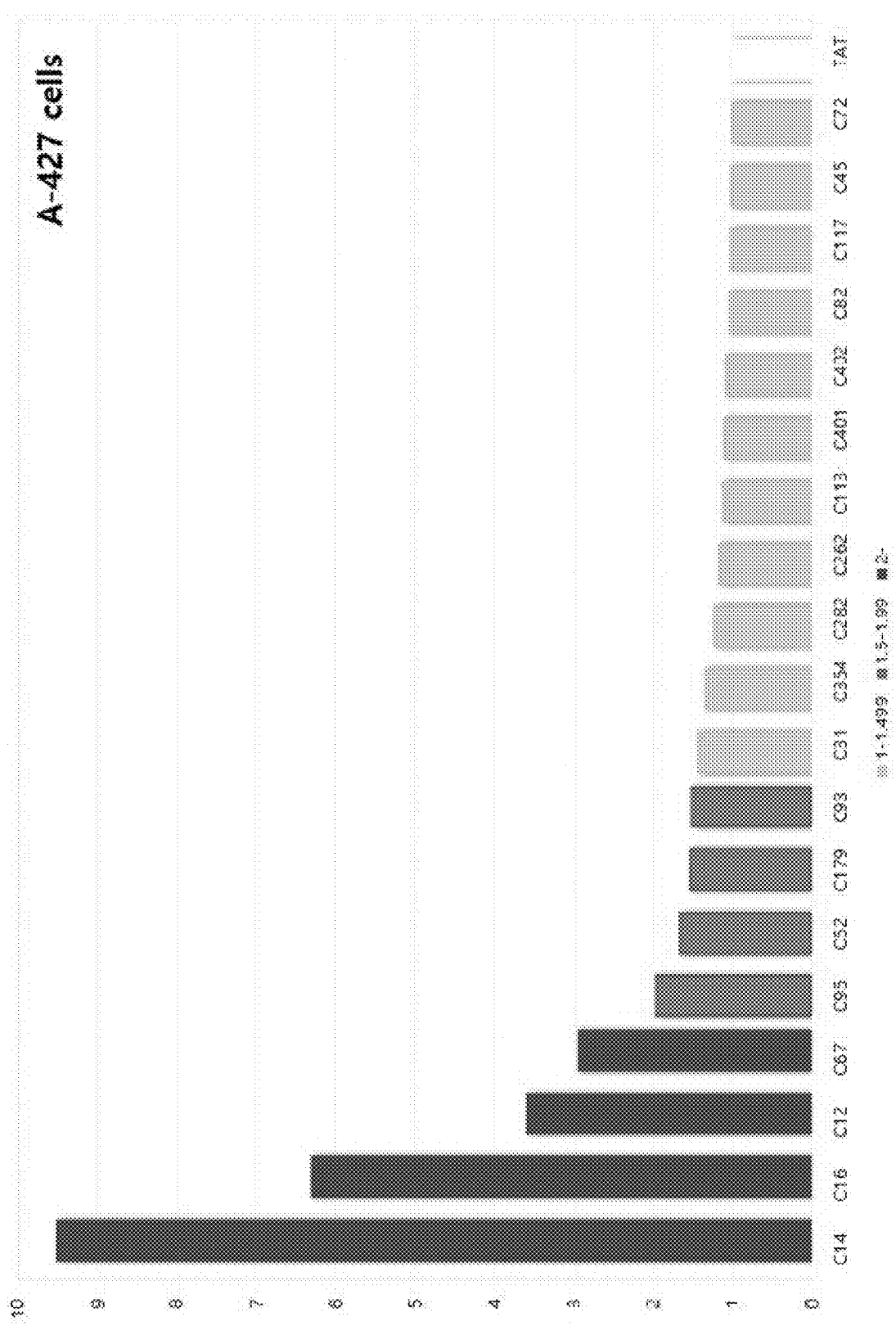
FIG. 16 is a graph of comparing CPP and TAT according to the present invention in lung cells (A-427 cells)

The cell permeability of the CPP according to the present invention for lung cells (A-427 cell line) is shown in FIG. 16. Compared with the conventional CPP, which is TAT, C14, C16, C12, C67, C95, C52, C179, C93, C31, C354, C282, C262, C113, C401, C402, C82, C117, C45, and C72 exhibited higher cell permeability in lung cells, and particularly, C14, C16, C12, and C67 exhibited 2-fold higher cell permeability than TAT, confirming that they are particularly suitable CPPs for the delivery of a biologically active material into lung cells or lung tissue.

5-10. Evaluation of Cell Penetration Efficiency Using Laryngeal Cells

Figure 17:
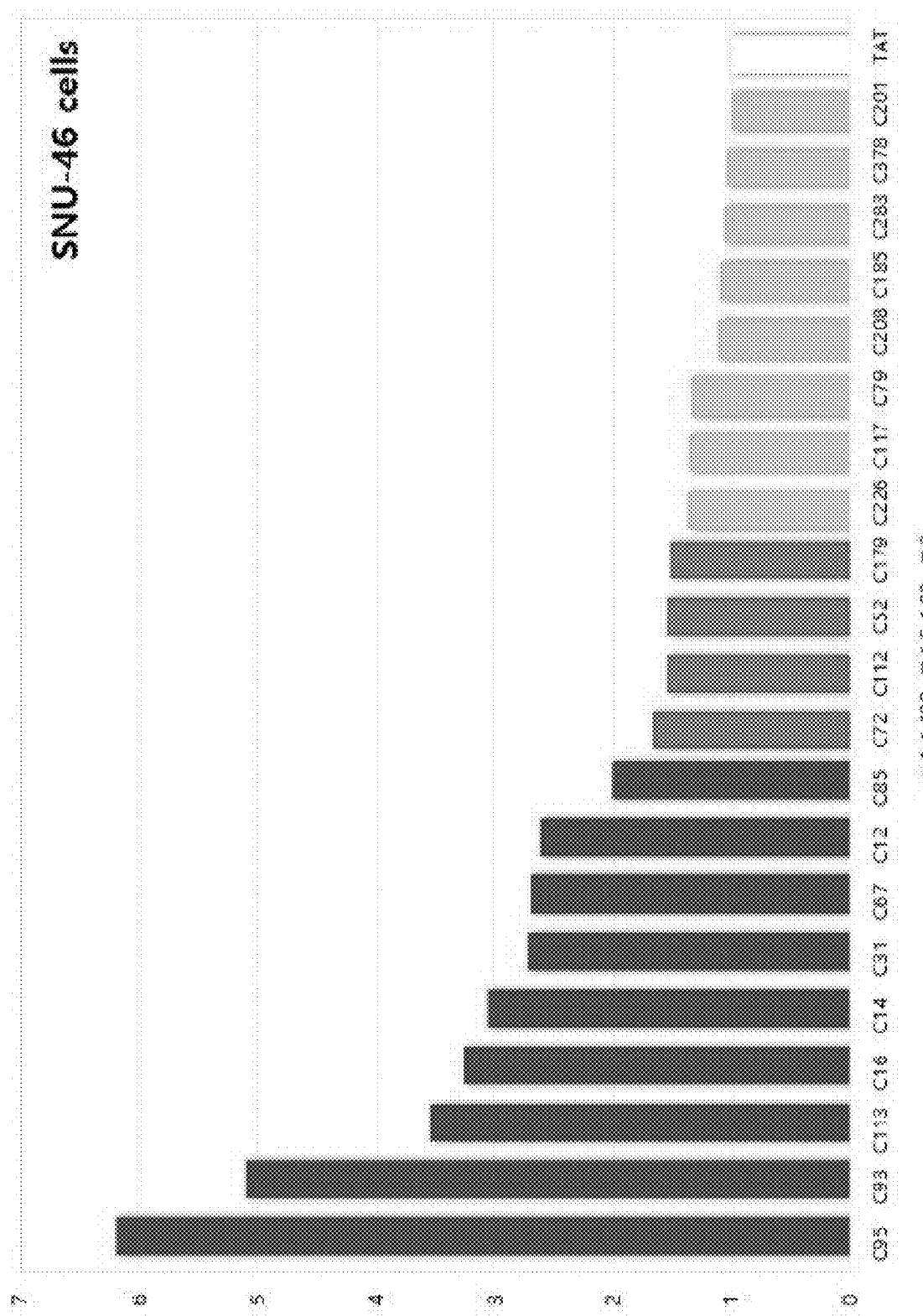
FIG. 17 is a graph of comparing CPP and TAT according to the present invention in laryngeal cells (SNU-46 cells).

The cell permeability of the CPP according to the present invention for laryngeal cells (SNU-46 cell line) is shown in FIG. 17. Compared with the conventional CPP, which is TAT, C95, C93, C113, C16, C14, C31, C67, C12, C85, C72, C112, C52, C179, C226, C117, C79, C208, C185, C283, C378, and C201 exhibited higher cell permeability in laryngeal cells, and particularly, C95, C93, C113, C16, C14, C31, C67, C12, and C85 exhibited 2-fold higher cell permeability than TAT, confirming that they are particularly suitable CPPs for the delivery of a biologically active material into laryngeal cells or laryngeal tissue.

Through the above examples, it was confirmed that most of the cationic CPPs effectively deliver a biologically active material into target cells. Particularly, C12, C14, C16, C31, C52, C67, C93, C95, C113, C179, C185, C72, C79, C112, C117, and C208 showed excellent cell permeability regardless of a cell type, and some exhibited superior cell permeability to the conventional CPP, which is TAT. In addition, since some CPPs exhibited particularly excellent cell permeability for specific types of cells or tissue, it is considered that suitable CPP is selected depending on a desired type of tissue to more effectively deliver a biologically active material.

Taken together, it was confirmed that the cationic CPPs newly found by the present inventors have significantly excellent cell permeability that allows a biologically active molecule to be delivered into cells, and can effectively maintain the activity of the biologically active molecule delivered into the cells. That is, the cationic CPPs according to the present invention can effectively deliver various active components into target cells, and thus can be applied in various fields such as beauty, diagnosis, and medical care.

A cell penetrating peptide (CPP) according to the present invention is a novel cationic cell penetrating peptide that can effectively transport a biologically active molecule by passing through a cell membrane even when a biologically active molecule is bound thereto, and compared with conventional CPPs, it has excellent cell permeability enabling the transport of a biologically active molecule into cells, and the delivered biologically active molecule can effectively maintain its activity in cells. Accordingly, the CPP of the present invention can be very useful in various fields including cosmetics, diagnostics, drug delivery systems, recombinant protein vaccines, DNA/RNA therapeutics, and gene and protein therapy.

It should be understood by those of ordinary skill in the art that the above descriptions of the present invention are exemplary, and the example embodiments disclosed herein can be easily modified into other specific forms without changing the technical spirit or essential features of the present invention. Therefore, it should be interpreted that the example embodiments described above are exemplary in all aspects, and are not limitative.

What is claimed is:

1. A method of delivering a biologically active molecule into a subject or cells, comprising:
   (S1) preparing a cell penetrating peptide;
   (S2) binding the biologically active molecule to the cell penetrating peptide to prepare a complex comprising the cell penetrating peptide and the biologically active molecule; and
   (S3) administering the complex into a subject or cells in need thereof,
   wherein the cell penetrating peptide consists of an amino acid sequence represented by General Formula below:
   $R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$,
   wherein in General Formula, $R_{14}$ is arginine (R), proline (P), lysine (K), or isoleucine (I);
   at least one of $R_1$ to $R_{14}$ is proline (P);
   when arginine (R) is assigned 1 point and lysine (K) is assigned 0.5 points among $R_1$ to $R_{14}$, the sum of the peptide is 6.5 points or more;
   the peptide includes one or more amino acids selected from the group consisting of valine (V), leucine (L), and isoleucine (I); and
   wherein the cell penetrating peptide consists of any one amino acid sequence selected from the group consisting of SEQ ID NOs: 1 to 53.

2. The method of claim 1, wherein the cell penetrating peptide has an α-helix structure.

3. The method of claim 1, wherein the cell penetrating peptide is cationic.

4. The method of claim 1, wherein the cell penetrating peptide further satisfies one or more characteristics selected from the group consisting of the following characteristics:
   (a) in General Formula, $R_5$-$R_6$ is any one set of consecutive amino acids selected from the group consisting of VI, KR, RL, KK, LR, RA, RK, and KQ;
   (b) $R_9$ and $R_{10}$ are each independently arginine (R), lysine (K), alanine (A), leucine (L), histidine (H), or tryptophan (W); and
   (c) $R_2$ is proline (P), leucine (L), arginine (R), lysine (K), valine (V), or alanine (A).

5. The method of claim 4, wherein the cell penetrating peptide further satisfies one or more characteristics selected from the group consisting of the following characteristics:
   (a) in General Formula, $R_4$ is lysine (K), leucine (L), arginine (R), or isoleucine (I); and
   (b) the peptide does not include glutamic acid (E), glycine (G), and tyrosine (Y).

6. The method of claim 1, wherein the cell penetrating peptide mediates the delivery of a biologically active molecule bound thereto into cells.

7. The method of claim 1, wherein the cells are one or more selected from the group consisting of blood-brain barrier endothelial cells, cancer cells, blood cells, epithelial cells, skin cells, epidermal cells, dermal fibroblasts, cervical cells, lymphocytes, immune cells, stem cells, induced pluripotent stem cells, neural stem cells, T cells, B cells, natural killer cells, macrophages, monocytes, microglia, neurons, glial cells, astrocytes, muscle cells, brain cells, hepatocytes, kidney cells, lung cells, and laryngeal cells.

8. The method of claim 1, wherein the cell penetrating peptide is bound to one or both ends of the biologically active molecule.

9. The method of claim 1, wherein one to five connected cell penetrating peptides are bound to one or both ends of the biologically active molecule.

10. The method of claim 1, wherein the binding is a chemical bond or a bond using a linker.

11. The method of claim 10, wherein the chemical bond is one or more selected from the group consisting of a disulfide bond, a diamine bond, a sulfide-amine bond, a carboxyl-amine bond, an ester bond, a diselenide bond, a maleimide bond, a thioester bond, a peptide bond, and a thioether bond.

12. The method of claim 1, wherein the biologically active molecule is one or more selected from the group consisting of peptides, proteins, glycoproteins, nucleic acids, carbohydrates, lipids, glycolipids, compounds, semi-synthetic drugs, microparticles, nanoparticles, liposomes, viruses, quantum dots, fluorochromes, and toxins.

13. The method of claim 12, wherein the protein is one or more selected from the group consisting of growth factors, enzymes, nucleases, transcription factors, antigenic peptides, antibodies, antibody fragments, hormones, carrier proteins, immunoglobulins, structural proteins, motor function proteins, receptors, signaling proteins, storage proteins, membrane proteins, transmembrane proteins, internal proteins, external proteins, secretory proteins, viral proteins, protein complexes, chemically modified proteins, and prions.

14. The method of claim 12, wherein the nucleic acid is one or more selected from the group consisting of DNA, RNA, an antisense oligonucleotide (ASO), microRNA (miRNA), small interfering RNA (siRNA), an aptamer, a locked nucleic acid (LNA), a peptide nucleic acid (PNA), and a morpholino.

15. The method of claim 12, wherein the compound is one or more selected from the group consisting of a therapeutic drug, a toxic compound, and a chemical compound.

* * * * *

```
                          SEQUENCE LISTING

Sequence total quantity: 74
SEQ ID NO: 1            moltype = AA  length = 14
FEATURE                 Location/Qualifiers
source                  1..14
                        mol_type = protein
                        organism = synthetic construct
SEQUENCE: 1
KPRKKKKRK NKKI                                                            14

SEQ ID NO: 2            moltype = AA  length = 14
FEATURE                 Location/Qualifiers
source                  1..14
                        mol_type = protein
                        organism = synthetic construct
SEQUENCE: 2
ALVLLRRRRR DRKP                                                           14

SEQ ID NO: 3            moltype = AA  length = 14
FEATURE                 Location/Qualifiers
source                  1..14
                        mol_type = protein
                        organism = synthetic construct
```

```
SEQUENCE: 3
RPRRKKQIKR LCKR                                                              14

SEQ ID NO: 4              moltype = AA   length = 14
FEATURE                   Location/Qualifiers
source                    1..14
                          mol_type = protein
                          organism = synthetic construct
SEQUENCE: 4
IRAKKKKRRR KKKP                                                              14

SEQ ID NO: 5              moltype = AA   length = 14
FEATURE                   Location/Qualifiers
source                    1..14
                          mol_type = protein
                          organism = synthetic construct
SEQUENCE: 5
TKRRKRRLRR RLTP                                                              14

SEQ ID NO: 6              moltype = AA   length = 14
FEATURE                   Location/Qualifiers
source                    1..14
                          mol_type = protein
                          organism = synthetic construct
SEQUENCE: 6
KKRKKRRKKR KVDP                                                              14

SEQ ID NO: 7              moltype = AA   length = 14
FEATURE                   Location/Qualifiers
source                    1..14
                          mol_type = protein
                          organism = synthetic construct
SEQUENCE: 7
ARLRVILRRR NPKR                                                              14

SEQ ID NO: 8              moltype = AA   length = 14
FEATURE                   Location/Qualifiers
source                    1..14
                          mol_type = protein
                          organism = synthetic construct
SEQUENCE: 8
ARLRVILRRR HPRR                                                              14

SEQ ID NO: 9              moltype = AA   length = 14
FEATURE                   Location/Qualifiers
source                    1..14
                          mol_type = protein
                          organism = synthetic construct
SEQUENCE: 9
WPRRRLRLRH RARR                                                              14

SEQ ID NO: 10             moltype = AA   length = 14
FEATURE                   Location/Qualifiers
source                    1..14
                          mol_type = protein
                          organism = synthetic construct
SEQUENCE: 10
LVPRRLRRRA RRRK                                                              14

SEQ ID NO: 11             moltype = AA   length = 14
FEATURE                   Location/Qualifiers
source                    1..14
                          mol_type = protein
                          organism = synthetic construct
SEQUENCE: 11
SRRRLRRFLR RIAP                                                              14

SEQ ID NO: 12             moltype = AA   length = 14
FEATURE                   Location/Qualifiers
source                    1..14
                          mol_type = protein
                          organism = synthetic construct
SEQUENCE: 12
AARIRALRRR RRRP                                                              14
```

```
SEQ ID NO: 13           moltype = AA   length = 14
FEATURE                 Location/Qualifiers
source                  1..14
                        mol_type = protein
                        organism = synthetic construct
SEQUENCE: 13
MPKIRKLKRR KKFR                                                          14

SEQ ID NO: 14           moltype = AA   length = 14
FEATURE                 Location/Qualifiers
source                  1..14
                        mol_type = protein
                        organism = synthetic construct
SEQUENCE: 14
IPLRRLMRRA RRHR                                                          14

SEQ ID NO: 15           moltype = AA   length = 14
FEATURE                 Location/Qualifiers
source                  1..14
                        mol_type = protein
                        organism = synthetic construct
SEQUENCE: 15
RPALKQRRWR RKKK                                                          14

SEQ ID NO: 16           moltype = AA   length = 14
FEATURE                 Location/Qualifiers
source                  1..14
                        mol_type = protein
                        organism = synthetic construct
SEQUENCE: 16
KRRKLRIKRR IRVP                                                          14

SEQ ID NO: 17           moltype = AA   length = 14
FEATURE                 Location/Qualifiers
source                  1..14
                        mol_type = protein
                        organism = synthetic construct
SEQUENCE: 17
RLRALVRRKQ RARP                                                          14

SEQ ID NO: 18           moltype = AA   length = 14
FEATURE                 Location/Qualifiers
source                  1..14
                        mol_type = protein
                        organism = synthetic construct
SEQUENCE: 18
LMPSKIRRRK KRKK                                                          14

SEQ ID NO: 19           moltype = AA   length = 14
FEATURE                 Location/Qualifiers
source                  1..14
                        mol_type = protein
                        organism = synthetic construct
SEQUENCE: 19
RPIRKLLRQA RQRR                                                          14

SEQ ID NO: 20           moltype = AA   length = 14
FEATURE                 Location/Qualifiers
source                  1..14
                        mol_type = protein
                        organism = synthetic construct
SEQUENCE: 20
MKRLLKVVRR RRRP                                                          14

SEQ ID NO: 21           moltype = AA   length = 14
FEATURE                 Location/Qualifiers
source                  1..14
                        mol_type = protein
                        organism = synthetic construct
SEQUENCE: 21
RVAALLRRRR RERP                                                          14

SEQ ID NO: 22           moltype = AA   length = 14
FEATURE                 Location/Qualifiers
source                  1..14
                        mol_type = protein
                        organism = synthetic construct
```

```
SEQUENCE: 22
RTRLLRRLRA LKPR                                                                    14

SEQ ID NO: 23         moltype = AA  length = 14
FEATURE               Location/Qualifiers
source                1..14
                      mol_type = protein
                      organism = synthetic construct
SEQUENCE: 23
RPLVRRRLRR AVRR                                                                    14

SEQ ID NO: 24         moltype = AA  length = 14
FEATURE               Location/Qualifiers
source                1..14
                      mol_type = protein
                      organism = synthetic construct
SEQUENCE: 24
YLRRKLRRRA GEPR                                                                    14

SEQ ID NO: 25         moltype = AA  length = 14
FEATURE               Location/Qualifiers
source                1..14
                      mol_type = protein
                      organism = synthetic construct
SEQUENCE: 25
RVRAILRRTR RKEP                                                                    14

SEQ ID NO: 26         moltype = AA  length = 14
FEATURE               Location/Qualifiers
source                1..14
                      mol_type = protein
                      organism = synthetic construct
SEQUENCE: 26
RVRALARRRR QARP                                                                    14

SEQ ID NO: 27         moltype = AA  length = 14
FEATURE               Location/Qualifiers
source                1..14
                      mol_type = protein
                      organism = synthetic construct
SEQUENCE: 27
YRPRRKKITK KLKR                                                                    14

SEQ ID NO: 28         moltype = AA  length = 14
FEATURE               Location/Qualifiers
source                1..14
                      mol_type = protein
                      organism = synthetic construct
SEQUENCE: 28
YRPRRKKATK KLKR                                                                    14

SEQ ID NO: 29         moltype = AA  length = 14
FEATURE               Location/Qualifiers
source                1..14
                      mol_type = protein
                      organism = synthetic construct
SEQUENCE: 29
RIRALARRRD RRRP                                                                    14

SEQ ID NO: 30         moltype = AA  length = 14
FEATURE               Location/Qualifiers
source                1..14
                      mol_type = protein
                      organism = synthetic construct
SEQUENCE: 30
RPRRKKQAKR LGKR                                                                    14

SEQ ID NO: 31         moltype = AA  length = 14
FEATURE               Location/Qualifiers
source                1..14
                      mol_type = protein
                      organism = synthetic construct
SEQUENCE: 31
RPRRKKQVKR IGKR                                                                    14
```

```
SEQ ID NO: 32              moltype = AA   length = 14
FEATURE                    Location/Qualifiers
source                     1..14
                           mol_type = protein
                           organism = synthetic construct SEQUENCE: 32
RVRTLLRRRR TERP                                                              14

SEQ ID NO: 33              moltype = AA   length = 14
FEATURE                    Location/Qualifiers
source                     1..14
                           mol_type = protein
                           organism = synthetic construct SEQUENCE: 33
ARRLRRRTAK LPAR                                                              14

SEQ ID NO: 34              moltype = AA   length = 14
FEATURE                    Location/Qualifiers
source                     1..14
                           mol_type = protein
                           organism = synthetic construct SEQUENCE: 34
KRKLKVRRKL REPR                                                              14

SEQ ID NO: 35              moltype = AA   length = 14
FEATURE                    Location/Qualifiers
source                     1..14
                           mol_type = protein
                           organism = synthetic construct SEQUENCE: 35
AIKRRRRRAL AKRP                                                              14

SEQ ID NO: 36              moltype = AA   length = 14
FEATURE                    Location/Qualifiers
source                     1..14
                           mol_type = protein
                           organism = synthetic construct SEQUENCE: 36
AVKRRRRRAL AKRP                                                              14

SEQ ID NO: 37              moltype = AA   length = 14
FEATURE                    Location/Qualifiers
source                     1..14
                           mol_type = protein
                           organism = synthetic construct SEQUENCE: 37
RPIRKLVRKA REKR                                                              14

SEQ ID NO: 38              moltype = AA   length = 14
FEATURE                    Location/Qualifiers
source                     1..14
                           mol_type = protein
                           organism = synthetic construct SEQUENCE: 38
RRALKRRAMR ARRP                                                              14

SEQ ID NO: 39              moltype = AA   length = 14
FEATURE                    Location/Qualifiers
source                     1..14
                           mol_type = protein
                           organism = synthetic construct SEQUENCE: 39
RRALRRRAQR RGAP                                                              14

SEQ ID NO: 40              moltype = AA   length = 14
FEATURE                    Location/Qualifiers
source                     1..14
                           mol_type = protein
                           organism = synthetic construct SEQUENCE: 40
KARARRILRR RETP                                                              14

SEQ ID NO: 41              moltype = AA   length = 14
FEATURE                    Location/Qualifiers
source                     1..14
                           mol_type = protein
                           organism = synthetic construct
```

-continued

```
SEQUENCE: 41
KARARRILRR REAP                                                          14

SEQ ID NO: 42          moltype = AA  length = 14
FEATURE                Location/Qualifiers
source                 1..14
                       mol_type = protein
                       organism = synthetic construct SEQUENCE: 42
RRKVVREKRK RKLP                                                          14

SEQ ID NO: 43          moltype = AA  length = 14
FEATURE                Location/Qualifiers
source                 1..14
                       mol_type = protein
                       organism = synthetic construct SEQUENCE: 43
RKVLPRKQKR KRVK                                                          14

SEQ ID NO: 44          moltype = AA  length = 14
FEATURE                Location/Qualifiers
source                 1..14
                       mol_type = protein
                       organism = synthetic construct SEQUENCE: 44
RLRAIRRRRR SLDP                                                          14

SEQ ID NO: 45          moltype = AA  length = 14
FEATURE                Location/Qualifiers
source                 1..14
                       mol_type = protein
                       organism = synthetic construct SEQUENCE: 45
ARVRARLRRR RIEP                                                          14

SEQ ID NO: 46          moltype = AA  length = 14
FEATURE                Location/Qualifiers
source                 1..14
                       mol_type = protein
                       organism = synthetic construct SEQUENCE: 46
RLREKRRSLK RKRP                                                          14

SEQ ID NO: 47          moltype = AA  length = 14
FEATURE                Location/Qualifiers
source                 1..14
                       mol_type = protein
                       organism = synthetic construct SEQUENCE: 47
RERKRANRKK LKKP                                                          14

SEQ ID NO: 48          moltype = AA  length = 14
FEATURE                Location/Qualifiers
source                 1..14
                       mol_type = protein
                       organism = synthetic construct SEQUENCE: 48
LRRVETLRRR KQPR                                                          14

SEQ ID NO: 49          moltype = AA  length = 14
FEATURE                Location/Qualifiers
source                 1..14
                       mol_type = protein
                       organism = synthetic construct SEQUENCE: 49
SVKRRRRRAL AKRP                                                          14

SEQ ID NO: 50          moltype = AA  length = 14
FEATURE                Location/Qualifiers
source                 1..14
                       mol_type = protein
                       organism = synthetic construct SEQUENCE: 50
RALRRRLHRQ RKLP                                                          14
```

| | | |
|---|---|---|
| SEQ ID NO: 51<br>FEATURE<br>source | moltype = AA   length = 14<br>Location/Qualifiers<br>1..14<br>mol_type = protein<br>organism = synthetic construct | |
| SEQUENCE: 51<br>RRREPLRARA RVRR | | 14 |
| SEQ ID NO: 52<br>FEATURE<br>source | moltype = AA   length = 14<br>Location/Qualifiers<br>1..14<br>mol_type = protein<br>organism = synthetic construct | |
| SEQUENCE: 52<br>RVRSLARRAR RRTP | | 14 |
| SEQ ID NO: 53<br>FEATURE<br>source | moltype = AA   length = 14<br>Location/Qualifiers<br>1..14<br>mol_type = protein<br>organism = synthetic construct | |
| SEQUENCE: 53<br>ARKNRMARQR RLRP | | 14 |
| SEQ ID NO: 54<br>FEATURE<br>source | moltype = AA   length = 14<br>Location/Qualifiers<br>1..14<br>mol_type = protein<br>organism = synthetic construct | |
| SEQUENCE: 54<br>RALRRRAARA ARRP | | 14 |
| SEQ ID NO: 55<br>FEATURE<br>source | moltype = AA   length = 14<br>Location/Qualifiers<br>1..14<br>mol_type = protein<br>organism = synthetic construct | |
| SEQUENCE: 55<br>RRRQRKEKVR NQKP | | 14 |
| SEQ ID NO: 56<br>FEATURE<br>source | moltype = AA   length = 14<br>Location/Qualifiers<br>1..14<br>mol_type = protein<br>organism = synthetic construct | |
| SEQUENCE: 56<br>RALKLRRRRR AVLP | | 14 |
| SEQ ID NO: 57<br>FEATURE<br>source | moltype = AA   length = 14<br>Location/Qualifiers<br>1..14<br>mol_type = protein<br>organism = synthetic construct | |
| SEQUENCE: 57<br>RERKRAARKK IKKP | | 14 |
| SEQ ID NO: 58<br>FEATURE<br>source | moltype = AA   length = 14<br>Location/Qualifiers<br>1..14<br>mol_type = protein<br>organism = synthetic construct | |
| SEQUENCE: 58<br>RLKEERLKKR RRSP | | 14 |
| SEQ ID NO: 59<br>FEATURE<br>source | moltype = AA   length = 14<br>Location/Qualifiers<br>1..14<br>mol_type = protein<br>organism = synthetic construct | |
| SEQUENCE: 59<br>LDRERRRKKA ERRP | | 14 |
| SEQ ID NO: 60<br>FEATURE<br>source | moltype = AA   length = 14<br>Location/Qualifiers<br>1..14<br>mol_type = protein<br>organism = synthetic construct | |

```
SEQUENCE: 60
RSPARKRVRA QKKR                                                    14

SEQ ID NO: 61           moltype = AA  length = 11
FEATURE                 Location/Qualifiers
source                  1..11
                        mol_type = protein
                        organism = synthetic construct
SEQUENCE: 61
YGRKKRRQRR R                                                       11

SEQ ID NO: 62           moltype = DNA  length = 42
FEATURE                 Location/Qualifiers
source                  1..42
                        mol_type = other DNA
                        organism = synthetic construct
SEQUENCE: 62
aaacctagaa agaaaagaa gaagcggaag aacaagaaga tc                      42

SEQ ID NO: 63           moltype = DNA  length = 42
FEATURE                 Location/Qualifiers
source                  1..42
                        mol_type = other DNA
                        organism = synthetic construct
SEQUENCE: 63
gccctggtgc tgctgagaag aagacggcgg gacagaaagc ct                     42

SEQ ID NO: 64           moltype = DNA  length = 42
FEATURE                 Location/Qualifiers
source                  1..42
                        mol_type = other DNA
                        organism = synthetic construct
SEQUENCE: 64
cggcctagaa gaaagaaaca gatcaagcgg ctgtgcaaga ga                     42

SEQ ID NO: 65           moltype = DNA  length = 42
FEATURE                 Location/Qualifiers
source                  1..42
                        mol_type = other DNA
                        organism = synthetic construct
SEQUENCE: 65
atcagagcca agaagaagaa aagacggaga aagaagaaac ct                     42

SEQ ID NO: 66           moltype = DNA  length = 42
FEATURE                 Location/Qualifiers
source                  1..42
                        mol_type = other DNA
                        organism = synthetic construct
SEQUENCE: 66
acaaagagac gcaagcggag actgagaaga cggctgaccc ct                     42

SEQ ID NO: 67           moltype = DNA  length = 42
FEATURE                 Location/Qualifiers
source                  1..42
                        mol_type = other DNA
                        organism = synthetic construct
SEQUENCE: 67
aaaaagagaa agaagcggag aaagaaaaga aggtggacc ct                      42

SEQ ID NO: 68           moltype = DNA  length = 42
FEATURE                 Location/Qualifiers
source                  1..42
                        mol_type = other DNA
                        organism = synthetic construct
SEQUENCE: 68
gccagactga gagtgatcct gcggagaaga aaccctaagc gg                     42

SEQ ID NO: 69           moltype = DNA  length = 42
FEATURE                 Location/Qualifiers
source                  1..42
                        mol_type = other DNA
                        organism = synthetic construct
SEQUENCE: 69
gccagactga gagtgatcct gcggagacgg caccctagac gc                     42
```

| SEQ ID NO: 70 | moltype = DNA length = 42 |
| FEATURE | Location/Qualifiers |
| source | 1..42 |
| | mol_type = other DNA |
| | organism = synthetic construct |

SEQUENCE: 70
tggcctagac ggcggctgag actgcggcac agagccagaa ga  42

| SEQ ID NO: 71 | moltype = DNA length = 42 |
| FEATURE | Location/Qualifiers |
| source | 1..42 |
| | mol_type = other DNA |
| | organism = synthetic construct |

SEQUENCE: 71
ctggtgccta gacggctgag acggcgggcc agaagaagaa ag  42

| SEQ ID NO: 72 | moltype = DNA length = 42 |
| FEATURE | Location/Qualifiers |
| source | 1..42 |
| | mol_type = other DNA |
| | organism = synthetic construct |

SEQUENCE: 72
agcagaagac ggctgcggag attcctgaga cgcatcgccc ct  42

| SEQ ID NO: 73 | moltype = DNA length = 42 |
| FEATURE | Location/Qualifiers |
| source | 1..42 |
| | mol_type = other DNA |
| | organism = synthetic construct |

SEQUENCE: 73
aaaagaagaa agctgagaat caagcggcgg atcagagtgc ct  42

| SEQ ID NO: 74 | moltype = DNA length = 42 |
| FEATURE | Location/Qualifiers |
| source | 1..42 |
| | mol_type = other DNA |
| | organism = synthetic construct |

SEQUENCE: 74
gccgctagaa tcagagccct gagaagacgg cggcggagac ct  42